United States Patent
Young et al.

(10) Patent No.: US 10,311,975 B2
(45) Date of Patent: Jun. 4, 2019

(54) RULES-BASED SYSTEM FOR CARE MANAGEMENT

(71) Applicant: SENIORLINK INCORPORATED, Boston, MA (US)

(72) Inventors: David Cort Young, Nashua, NH (US); Thomas Matthew Grace, Stratham, NH (US)

(73) Assignee: SENIORLINK INCORPORATED, Boston, MA (US)

( * ) Notice: Subject to any disclaimer, the term of this patent is extended or adjusted under 35 U.S.C. 154(b) by 70 days.

(21) Appl. No.: 14/166,374

(22) Filed: Jan. 28, 2014

(65) Prior Publication Data

US 2014/0214441 A1 Jul. 31, 2014

Related U.S. Application Data

(60) Provisional application No. 61/757,454, filed on Jan. 28, 2013.

(51) Int. Cl.
*G16H 50/30* (2018.01)
*G16H 10/20* (2018.01)
*G16H 50/20* (2018.01)

(52) U.S. Cl.
CPC ............. *G16H 50/30* (2018.01); *G16H 10/20* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 7,319,970 B1* | 1/2008 | Simone | G06F 19/328 705/4 |
| 7,493,264 B1* | 2/2009 | Kelly | G06Q 10/06 705/2 |
| 2002/0019747 A1* | 2/2002 | Ware | G06Q 40/08 705/2 |

(Continued)

FOREIGN PATENT DOCUMENTS

| | | |
|---|---|---|
| EP | 1072994 A2 | 1/2001 |
| WO | 01/66007 A1 | 9/2001 |

(Continued)

*Primary Examiner* — Michael Tomaszewski
(74) *Attorney, Agent, or Firm* — Nelson Mullins Riley & Scarborough LLP; Anthony A. Laurentano

(57) ABSTRACT

A care management system for improving the care of a client who is supported by a caregiver is described. The caregiver may participate in regular activities with the client and record these activities in the care management system. The care management system may present the caregiver with questions on a regular basis. Information may also be input into the system by a care management team made up of professionals responsible for the client's overall care. A risk analyzer may determine the client's risk for different risk conditions, and may calculate domain-specific and overall risk scores for the client. Furthermore, the risk analyzer may make recommendations for actions to be taken by the client, the caregiver, or the care management team in order to improve the client's care. The information in the care management system may be used by the care management team to direct aspects of the client's care.

13 Claims, 24 Drawing Sheets

Overall Workflow

(56) References Cited

U.S. PATENT DOCUMENTS

| | | | |
|---|---|---|---|
| 2003/0004788 A1* | 1/2003 | Edmundson | G06Q 50/22 705/2 |
| 2005/0203773 A1* | 9/2005 | Soto | G06Q 40/08 705/2 |
| 2011/0060604 A1* | 3/2011 | Bangara | G06Q 10/10 705/2 |
| 2012/0078062 A1 | 3/2012 | Bagchi et al. | |
| 2013/0262357 A1* | 10/2013 | Amarasingham | G06F 19/00 706/21 |

FOREIGN PATENT DOCUMENTS

| | | |
|---|---|---|
| WO | 01/73526 A2 | 10/2001 |
| WO | 2009/132992 A2 | 11/2009 |

\* cited by examiner

Caregiver Sally Jones

Dashboard  Settings  Logout

MONTHLY HOME VISIT

Ethel Jones

October 2012

- Functional Assessment ✓
- Medical Assessment ✗
- Psychosocial-Behavioral ■
- Family-Community Supports ■
- Environment ■

Functional Assessment

Have there been any changes in ADLs?    NO    YES

| Bathing<br>Limited Assistance | Personal Hygiene<br>Total Dependence | Dressing (Upper)<br>Total Dependence | Locomotion (In)<br>Extensive Assistance | Transfers<br>Activity Did Not Occur |
| Eating<br>Total Dependence | Toileting<br>Supervision | Dressing (Lower)<br>Maximal Assistance | Locomotion (Out)<br>Total Dependence | Mobility<br>Setup Help Only |

Back    Next    Complete 412
414
410

Edit note                                    January 27, 2013

Note

Per 8/13 ST note from CG: Went to emergency for extreme pain in right foot. could not walk on it at all. X-ray showed no break... thought to be a sprain, was given pain medication and sent home.... A few hours later while at home mom started to feel very sick to her stomach... didn't get any better seemed to get worse so called for assistance again this time the paramedics founf her blood pressure very low and hear rate very high. They rushed her right in. It was determined that her potassium was very high. This became critical as she is a dialysis patient!!! She responded to all that was done to get it lowered. She was admitted then dialyzed at the hospital. She will be monitored thru the night in critical care unit to see if her levels are being maintained. The pain is no longer a priority. Will follow up tomorrow with her foot as her situation permits.

Cancel ❌                                        Save ✓

Caregiver
Sally Jones

Dashboard Settings Logout

MONTHLY HOME VISIT     OCTOBER 2012

Ethel Jones
Age 62
Branch Boston 1
Account AFC/Level 2
Placed 08/21/2011
Status Place Functional ✓
Medical ✗
Psychosocial-Behavioral ■
Family-Community Supports ■
Environment ■

Falls Assessment:    step 1 · step 2    *716*

○ None of minimal gait problems    ○ Unsteady Gait

History of Bone Fractures or weakness?
◉ No History, Diagnosis or Medication    ○ Positive History, Diagnosis or Medication Coagulants
◉ No Blood Thinners    ○ On Blood Thinners Post Surgical Risk
◉ No Post Surgical    ○ Post Surgical for recent abdominal, thoracic of LE Operation Back    Next    Complete    *716*

Care Manager

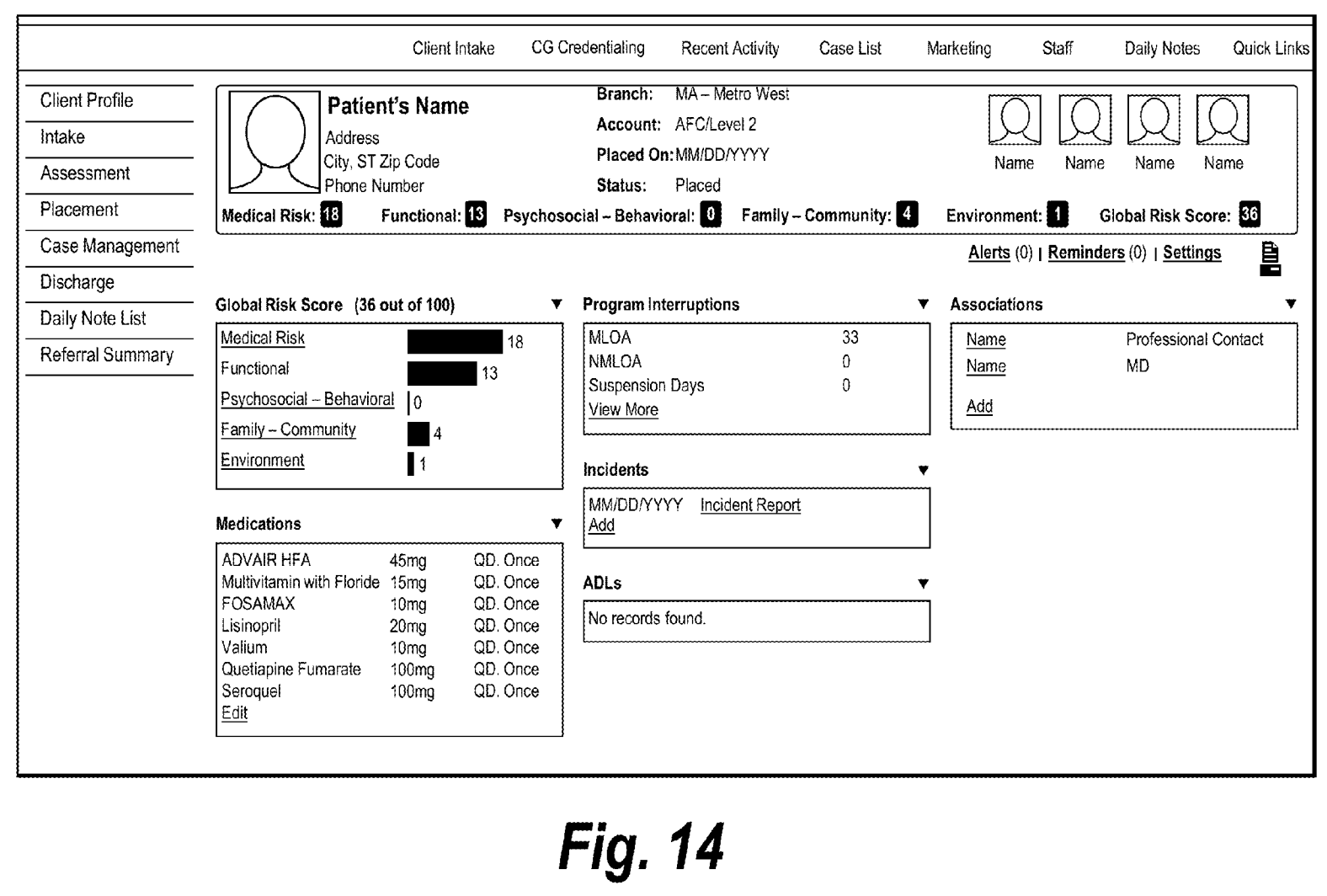

| | Client Intake | CG Credentialing | Recent Activity | Case List | Marketing | Staff | Daily Notes | Quick Links |
|---|---|---|---|---|---|---|---|---|

Client Profile
Intake
Assessment
Placement
Case Management
Discharge
Daily Note List
Referral Summary Patient's Name
Address
City, ST Zip Code
Phone Number Branch: MA – Metro West
Account: AFC/Level 2
Placed On: MM/DD/YYYY
Status: Placed Name   Name   Name   Name Medical Risk: 18   Functional: 13   Psychosocial – Behavioral: 0   Family – Community: 4   Environment: 1   Global Risk Score: 36

Alerts (0) | Reminders (0) | Settings

Global Risk Score (36 out of 100)

Medical Risk — 18
Functional — 13
Psychosocial – Behavioral — 0
Family – Community — 4
Environment — 1

▶ Program Interruptions

MLOA   33
NMLOA   0
Suspension Days   0
View More

▶ Incidents

MM/DD/YYYY   Incident Report
Add

▶ ADLs

No records found.

Associations

Name     Professional Contact
Name     MD
Add

Medications

ADVAIR HFA              45mg     QD. Once
Multivitamin with Floride 15mg    QD. Once
FOSAMAX                 10mg     QD. Once
Lisinopril               20mg     QD. Once
Valium                  10mg     QD. Once
Quetiapine Fumarate     100mg    QD. Once
Seroquel                100mg    QD. Once
Edit

*Fig. 14*

RULES-BASED SYSTEM FOR CARE MANAGEMENT

BACKGROUND

Some individuals (referred to herein as "clients") may require managed care, for example as a result of aging or disability. As used herein, "managed care" refers to care or supervision for an individual that is administered, supervised, or directed by another person or group of people, which may include professional caregivers and/or laymen. The present application relates to a method, medium, and system for managing the care of such an individual or group of individuals.

In some cases, the client may require extensive managed care that can only be provided in a dedicated managed care facility such as a nursing home. However, such facilities may be expensive and may limit the independence of the client housed in the facility. Therefore, in some situations it may be preferable for the client to receive at-home care (either in their own home, or in the home of a caregiver such as a relative or friend).

There remain a number of potential problems with providing at-home care for a client requiring managed care. For example, a lay caregiver may not recognize medically important events that could indicate the presence of a problem requiring expert attention. The lay caregiver may simply not know which of the many events in the client's daily routine carry medical significance and which do not.

On the other hand, if the client does see experts such as registered nurses or doctors in an at-home care situation, then the experts are unlikely to have access to the client on a 24/7 basis (in contrast to a managed care facility). Thus, the experts may not become aware of problems until these problems have escalated. This may increase the cost of the client's care and/or may increase the risk of negative outcomes, such as injury, hospitalization, or the removal of the client from at-home care.

SUMMARY

Exemplary embodiments provide a care management procedure and system that may improve the care of a client who is supported by a caregiver. According to exemplary embodiments, a procedure may be performed for providing ongoing care to a client and entering information related to the ongoing care into the care management system using an interface of the care management system. The care management system may guide a lay caregiver so that the lay caregiver provides information that may indicate the presence of a relevant condition (e.g., a condition that is relevant medically, psychologically, etc.).

The caregiver may participate in regular (e.g., daily) activities with the client and record these activities in an activity log in the care management system. Furthermore, the care management system may present the caregiver with questions (either general health-related questions or client-specific questions related to known conditions associated with the client) on a regular basis (e.g., daily). Still further, the caregiver may be given the opportunity to provide free-form notes about the client's daily activities.

Information may also be input into the system by a care management team comprising professionals responsible for the client's overall care and well-being. The care management team may include, for example, doctors, social workers, nurses, and a care manager who oversees the client's care.

Based on the information stored in the system and/or a profile of the client (compiled, e.g., by the care management team), a risk analyzer may determine the client's risk for different conditions across a number of domains (e.g., medical, behavioral, functional, environmental, community, etc.). The risk analyzer may analyze the answers to the questions directed to the caregiver as well as assessments performed by the care management team members, and may determine whether additional follow-up questions are necessary. Furthermore, the risk analyzer may perform a lexical analysis on the free-form notes written by the caregiver and/or care team members.

Based on the results of the risk analysis, domain-specific and overall risk scores may be calculated for the client. Furthermore, the risk analyzer may make recommendations for actions to be taken by the client, the caregiver, or the care management team in order to improve the client's care.

The information in the care management system may be used by the care management team to direct aspects of the client's care and make decisions regarding the client. The use of the care management system therefore affords the care management team a much deeper understanding of the client's daily activities. Furthermore, because the care management system may be programmed to filter medically relevant information from the extensive list of daily activities, the care management team may efficiently use the information in the care management system to direct the client's care.

To support the care management system, a workflow process may be performed in order to initially populate a database with client information, select questions that may be applicable to the client based on known conditions associated with the client or conditions for which the client may be at risk, train the caregiver in the use of the care management system, and determine whether certain clients are not suitable for the care management system. Regular care management may then be provided and recorded in the care management system.

Using the care management system described herein, the quality of a client's care may be improved, while still allowing the client a significantly greater degree of independence while concomitantly reducing the expense of ongoing care.

BRIEF DESCRIPTION OF THE DRAWINGS

The present invention will be better understood with reference to the following Figures depicting exemplary embodiments:

FIGS. 4A-4B are exemplary interfaces for the care management system as viewed by a caregiver upon logging into the care management system.

FIGS. 5A-5B depict exemplary interfaces for adding notes and quick notes, respectively.

FIGS. 7A-7D depict exemplary interfaces used to enter, record, and view information relating to an example of the risk of a fall by a client.

FIG. 8 depicts an exemplary interface for the care management system as viewed by a registered nurse upon logging into the system for a scheduled monthly visit.

Figure 13:
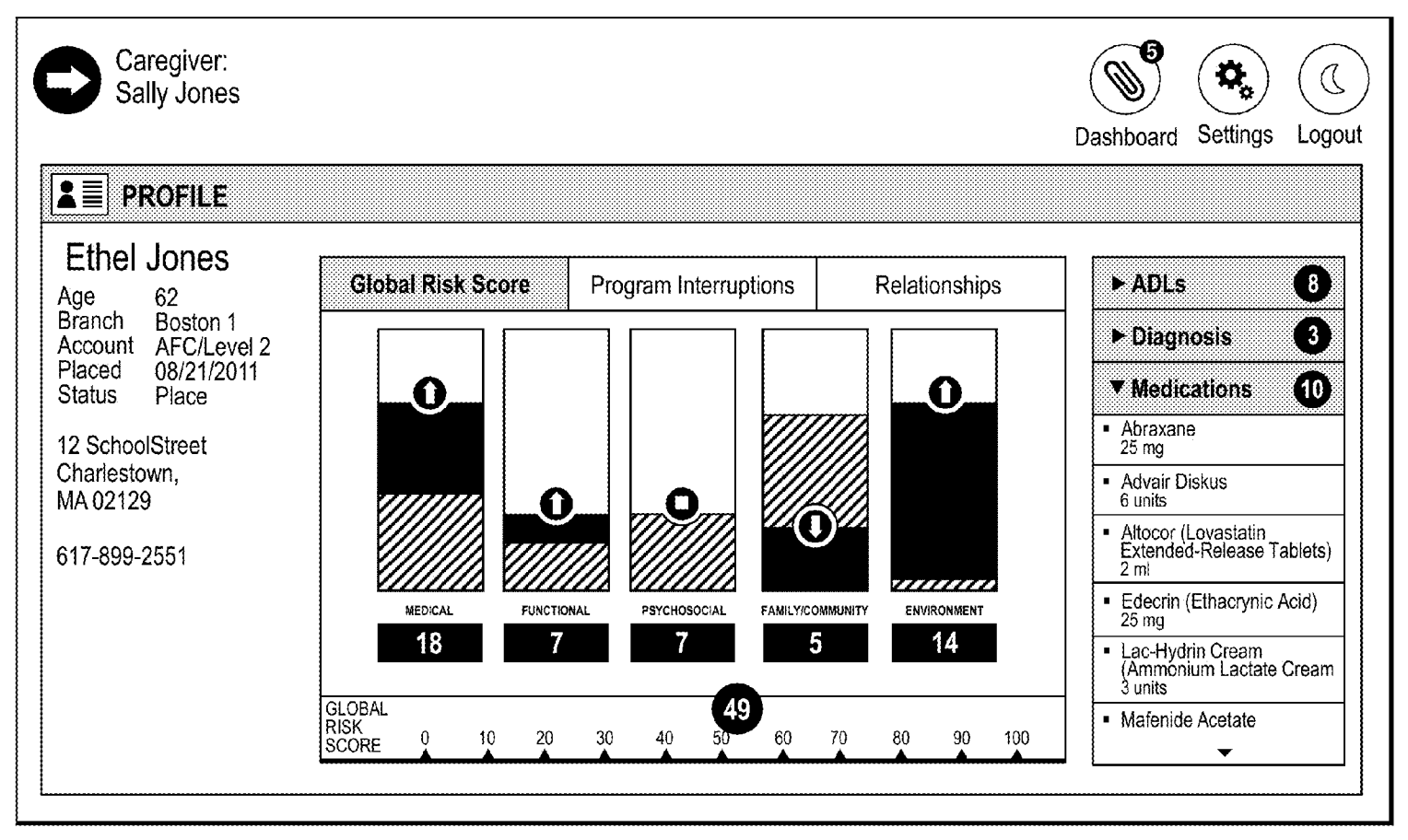

FIG. 13 is an exemplary interface for displaying risk scores as calculated by a risk analyzer.

FIG. 14 is an exemplary summary interface for displaying client information from the care management system.

DETAILED DESCRIPTION

Figure 1:
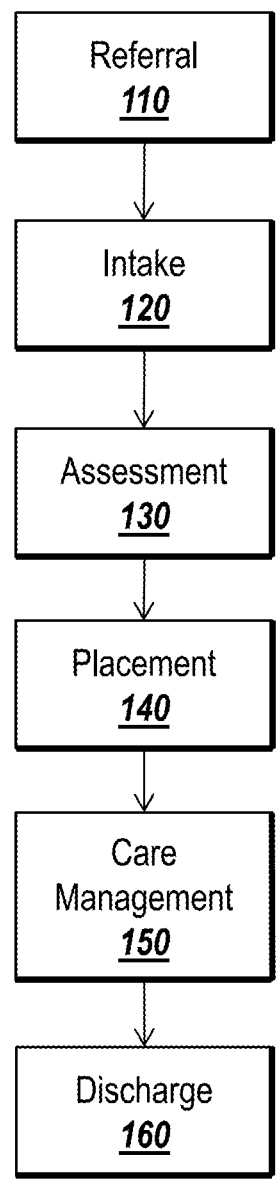
FIG. 1 depicts an exemplary workflow for managing the care of a client.

In many cases, although a client requires more care than they can provide for themselves, the client does not require full-time managed care. For example, the client may be able to rely on a friend or relative to act as a caregiver for the client in the client's (or caregiver's) own home.

Such a caregiver may be capable of performing some tasks to assist the client (e.g., helping the client bathe and/or dress, reminding the client to take medications, monitoring the client's food intake, etc.). However, such a caregiver rarely has formal medical or professional training relating to managed care. Although the caregiver may be able to monitor the client's actions and condition on a daily basis, the caregiver may not be aware that these actions or conditions may have medical significance and/or may be related to risk factors for negative outcomes (e.g., death, disability, or transfer of the client into a full-time managed care facility).

Thus, it is still necessary to rely on experts, such as doctors, registered nurses, social workers, etc., in order to provide comprehensive care for the client. Unfortunately, the time and resources of these experts is limited. Such experts may only be able to see the client on an as-needed basis, or on regularly scheduled visits at relatively long intervals.

Because the experts may see the client on only a limited basis, these experts may not have access to the kind of detailed information about the client's health status and regular daily activities that the client's dedicated caregiver may have. However, the caregiver may not be aware that the client's daily activities are of medical significance, and indeed may not know what information to record even if the caregiver wished to give the experts a window into the client's status.

Therefore, in an attempt to provide medically relevant information to the experts, the caregiver may provide far too much information about the client's status, or may omit information that the caregiver does not deem to be relevant (but which could indicate problems or client conditions to a trained expert). Thus, important information may be missed by the experts because the caregiver provided too much irrelevant information, thereby obscuring the relevant information, or important information may not be provided to the experts in the first place.

Accordingly, the overall care provided to the client by a caregiver and team of experts in a home-based situation may not be as coordinated, efficient, and/or effective as the client might receive at a full-time managed care facility, where a dedicated staff of experts may monitor the client on a daily basis.

The present application describes methods, systems, and mediums for use in providing care management. According to an exemplary embodiment, an exemplary workflow may be employed in order to generate information relevant to the care of the client. The workflow may involve regular (e.g., daily) activities by a dedicated caregiver and less frequent (e.g., monthly) activities by other members of the client's care management team (e.g., doctors, nurses, social workers, and a care manager who oversees the care of the client).

The system may prompt the caregiver to answer questions from a question library at determined intervals. The questions may be calibrated, timed, and/or triggered to provide useful insights to the client's care management team. Alternatively or in addition to the questions, members of the client's care management team may provide freeform notes, which may be parsed or analyzed for indications of a change in the client's condition and/or risk factors.

Based on the answers to the questions and/or the analysis of the freeform notes, a risk analyzer may calculate risk scores for different categories or "domains" of care. An overall risk score encompassing all domains may also be calculated. Any changes in the individual or overall risk scores over time may be noted by the system and may trigger warnings indicating that some action or intervention should occur (or at least should be considered) by the care management team.

Members of the care management team may interact with the care management system to monitor the client's condition and determine courses of action for the client's care. Using the care management system, it may be possible to avoid the expense and limited independence that may result from sending the client to a full-time managed care facility.

Overall Workflow

According to an exemplary embodiment, a workflow process may be carried out for a care management program (referred to herein as the "program"), as shown in FIG. 1. The workflow process may serve to organize or structure the activities of key actors in the care management system. Furthermore, the workflow process may provide or supplement data for a risk analyzer (described in more detail with respect to FIG. 2). The data may provide assessment data points that are stored, used, updated, and re-used to provide real-time evaluations of a client's condition.

The workflow may be manifested as an event-driven architecture that moves users through tasks and steps for completion. At each interdependent stage, users may be prompted to complete workflow tasks. In some embodiments, the care management system may restrict a user's ability to perform some workflow stages until prerequisite tasks are performed. The risk analyzer may adjust workflow and tasks dynamically as data about a client and a caregiver becomes, over time, broader and deeper.

Moreover, the risk analyzer may take into account sentinel events. A sentinel event is an event that may occur during the care of the client which is associated with a high risk (e.g., a risk above a predetermined threshold amount) of a negative health outcome, such as injury, hospitalization, discharge from the care management system into a fully managed care situation, or death. As sentinel events occur in many of the workflow stages, the risk analyzer may use the most current data available to perform fresh analyses, prompt for more information, and return up-to-date intelligence used by providers to craft the most efficient and effective care possible at a given stage of the workflow process.

In one exemplary embodiment, the workflow process may be divided into 6 workflow steps as shown in FIG. 1. Each step may contain tasks that are performed in series or in parallel. In one embodiment, all tasks in a given workflow step must be completed before the next workflow stage may begin.

At step 110 of the workflow process, a client may be referred to the care management system, for example by a doctor, psychologist, social worker, etc. The referral may be the result of a regular checkup of the client, or may be the result of a traumatic event (e.g., a brain injury, broken bone, etc.).

During the referral step 110, an initial record may be established in the care management system for the client. The initial record may be populated with basic information about the patient, potentially retrieved from external systems such as the client's electronic records. Such basic information may include, for example, contact information, demographics, basic descriptors of the client's inquiry, needs, etc. In order to create the initial record, the client may be provided with consent forms allowing the care management system to retrieve the client's pertinent information.

The initial record may include a status identifier for the client indicating in which step of the workflow process the client is currently participating.

Further, the client's financial eligibility may be confirmed during the referral step 110. For example, the client's insurance information may be retrieved and checked to verify that the client qualifies for the care management provided by the exemplary care management system. Steps for confirming the client's financial eligibility may vary according to local practices and laws.

Still further, the client may be screened for clinical eligibility. For example, if the client has a medical condition that would be best treated in a hospital or fully-managed-care environment, the client may be referred to such an environment.

Moreover, an initial risk stratification for the client may be derived from known information (e.g., whether the client at an increased risk for falls, what the client's overall risk for a negative outcome is estimated to be, etc.). The initial risk stratification may be used by the risk analyzer to determine a level of care required for the client and to select members of the client's care management team (e.g., based on the team members' experience or qualifications to address certain types of risks).

As part of the referral, or afterwards during the intake process 120, a caregiver and/or an alternative caregiver for the client may be identified. The caregiver may be, for example, a friend or relative of the client who agrees to regularly (e.g., daily) oversee the activities of the client. This may involve, for example, having the caregiver live with the client. As part of the referral process 110, a background check may be performed on the client and/or the caregiver(s).

Once the requisite actions are performed during the referral process 110, the client's status identifier may be updated and an initial intake process 120 may occur. During the intake process 120, the caregiver may be assessed to determine whether the caregiver will be able to provide adequate care for the client outside of a managed care facility. If the caregiver is unable to provide adequate care for the client, then it may be necessary to reject the client and caregiver, and recommend that the client be enrolled in an alternate support setting such as a full-time managed care facility.

During the intake process 120, information about the caregiver may be collected in order to assess the caretaker's ability to provide care for the client. For example, the caretaker may be evaluated for ability to perform the activities required by the client to be maintained at home. The intake process 120 may be carried out by a non-professional, staff member, or a care manager who is assigned to oversee the management of the care of the client through the care management system. The intake process 120 may involve sending the overseer for an at-home visit at the client's or caregiver's home.

During the intake process 120, paperwork may be collected such as a background check for the client and/or caregiver(s), a physician summary form, reference forms, a caregiver health form, and alternate caregiver information. This paperwork may be scanned and stored electronically in a data storage mechanism of the care management system.

At the end of the intake process 120, the overseer may determine whether the client is ready to proceed to a full assessment. If the determination is "yes," then the care management system may store an updated status for the client and a client assessment process 130 may then be performed.

The assessment process 130 may provide a comprehensive assessment of the strengths and needs of both the caregiver and the client. A rationale and documentation for an application to provide care may be created. Upon approval of the application, an initial client/caregiver-centered care plan may be prepared.

The assessment process 130 may be carried out by members of a care management team assigned to the client, such as a registered nurse, a doctor, a social worker, or a care manager, or a combination of members of the care management team. During the client assessment process, information relating to the client may be collected in order to initially populate the care management system with information relevant to the client's current status and ongoing care. Such client specific information can include, for example, age, gender, marital status, race/ethnicity, weight, height, diagnosis of the client, and the like. This information may be used in conjunction with statistical risk models in order to determine the client's risk for a variety of conditions.

The client assessment process 130 may involve sending members of the care management team to visit a proposed location at which care of the client will occur (e.g., the client's home or the caregiver's home). The proposed location may be evaluated for suitability and potential dangers or risks.

Different tasks within the client assessment process 130 may performed by different experts who are well-suited to the tasks. For example, a registered nurse (RN) may perform a medical and functional assessment of the client, while a care manager conducts a home/environment assessment.

In one embodiment, a registered nurse may evaluate the following items and may enter the results of the evaluation as inputs into the care management system: a basic functional assessment (such as the "Minimum Data Set-Home Care" or "MDS-HC" assessment), an updated determination of clinical eligibility, an assessment of the caregiver's competency, a medication list with side effects, an assessment of the client's risk for falling, and any notes the registered nurse believes may be relevant to the ongoing care of the patient.

In one embodiment, a care manager may evaluate the following items and may enter the results of the evaluation as inputs into the care management system: a home/environment assessment, an indication of any modifications required for the safe placement of the client in the home, and an updated risk assessment. The care manager may also review instructional information with the caregiver and the client.

As part of the assessment step 130, a care management team may be assembled and identifying information for the care management team may be saved in the care management system. The team may identify any potential problems or red flags for the management of the care of the client and may conduct an "at-risk" conference if needed. Information related to the potential problems or the at-risk conference may be stored in the care management system.

The first three steps of the workflow (Referral 110, Intake 120, and Assessment 130) serve a number of purposes. First, clients who are not suitable for care managed by a caregiver and the care management system may be filtered out of the program and towards more suitable care settings. For example, if it is determined during the first three steps of the process that the client or caregiver is unsuitable for the program and would be better suited to a managed care facility, then the relationship with the client may be ended and the client may be referred to such a facility.

Second, the first three steps of the workflow allow basic information about the client to be collected and entered into the care management system. The basic information may be organized into a profile specific to a particular client, which describes the client's status and risk factors. Based on the initial information provided to the care management system, an initial course of care may be determined and suitable questions about the client's daily activities may be selected. This allows the care management system to better tailor a course of care to the specific needs of individual clients.

Third, the first three steps of the workflow allow the care management team to "credential" the caregiver. That is, the caregiver may be trained in the use of the care management system and in providing care for the client in general.

Once it has been determined that a client/caregiver are suitable for the program and initial client information is populated to the care management system, a placement step 140 may occur. The placement step 140 may serve to provide a smooth transition into the care management system for the caregiver and the client. The caregiver and client may be provided with instruction in how to use the care management system.

Further, the placement step 140 may allow the care management team to confirm any rules and expectations with the client and caregiver, and to review the initial care plan for the client.

During the placement step 140, one or more members of the care management team may assist the caregiver in setting up the location in which care of the client will occur. This location may be, for example, the client's home or the caregiver's home. The placement step 140 may involve setting up one or more electronic devices embodying the care management system and training the caregiver to use the care management system.

Any information that was entered into the care management system at steps 110-130, such as the client's health status and medication list, may be reviewed during the placement step 140 and updated as necessary. Upon completion of the placement step, an initial report encompassing the information entered into the care management system to this point may be generated and provided to the client's primary care physician (PCP).

At step 150, the caregiver and care management team may now utilize the care management system to manage the ongoing care of the client. Steps 110-140 focus, from the perspective of the care management system and risk analyzer, on capturing an initial data set by performing tasks that are generally done only once (or a few times, in the case of updated information). In contrast, at the care management step 150, the caregiver may provide daily updates to the care management system in the form of answers to questions and freeform notes, among other possibilities. The care management team may make regular (e.g., monthly) visits to the location of the client, and/or may visit the client on an as-needed basis. Thus, during the care management step 150, the initial data set is continuously verified, extended, and updated.

A unique aspect of the care management step 150 is that, during this step, the care management system may harvest this data, acquired from a plurality of users in different fields of expertise, in real-time or near-real-time manner. This data may come from questions posed by the care management system during regular interviews of the caregiver and/or care management team.

A further unique aspect of the care management step 150 is that the data is acquired across multiple domains that contribute to risk and negative outcomes. A still further unique aspect of the care management step 150 is that, during this step, the care management system estimates the risks and predicts negative outcomes, and derives a client-specific care plan to guide and enhance the care of the client.

Some of the goals of the care management step 150 include managing the care process of the client, monitoring the care of the client, adjusting the client's care using (in part) risk data computed by the risk analyzer of the care management system, and preventing problems that might lead to decreased client satisfaction, negative impacts on client health, and/or increased cost.

The care management step 150 may involve a number of tasks that are repeated on both a predetermined and an ad-hoc basis (as determined during the course of the client's care by the care management system, based in part on answers to questions posed to the caregiver and the care management team).

One such task may include generating a client-specific care plan. The care management system may first generate a short-term (e.g., 30 day) initial care plan. In order to generate the short-term initial care plan, the risk analyzer of the care management system may perform an initial risk analysis (details of the risk analysis are discussed below in the detailed discussion of the risk analyzer and the question library) in order to identify domains that may carry increased risk for the client. The initial care plan may be generated based on the data obtained at steps 110-130.

The initial care plan may include a number of steps to be performed by the care giver and/or by members of the care management team. During the period in which the initial care plan is in place, the care management system may pose questions, as described in more detail below, about the status of the client and the client's environment. For example, the risk analyzer of the care management system may provide prompts and cues using one or more algorithms or regression models in order to obtain a more detailed picture of the client and the client's care. Based on the information obtained from these prompts and cues, the client's care plan may be updated on a regular basis (e.g., every 180 days and more frequently if the risk analyzer calculates an increased level of risk for a particular negative outcome).

During the care management step 150, the client's care management team may maintain regular in-home contact with the client and/or the caregiver. For example, the care management team may conduct at-home visits on a regular basis, on an ad-hoc basis, and on an unannounced basis.

Regular at-home visits may be performed at predetermined intervals, which may be consistent with best practice guidelines and/or regulatory requirements. Home visits may be associated with a procedure programmed into the care management system for performing a series of tasks. Using prompts and cues, the care management system may guide the members of the care management team through the tasks. Updates on sentinel events and the client's health and environmental status may be captured as structured data. This structured data may be used to update risk scores and trigger context-sensitive cues and prompts directed to improving the care plan of the client.

Ad hoc home visits may occur on an as-needed basis and/or after the occurrence of a triggering event. For example, the care management system may prompt an ad hoc home visit for a client with a moderate or high risk of re-hospitalization within 30 days following the client's discharge from a hospital. The risk analyzer may include algorithms and business rules for stratifying the client's risk for a negative outcome (e.g., into low, medium, and high strata). Furthermore, the care management system may include an incident tracking module/algorithm that harvests and store key data points regarding incidents such as an injurious fall, hospitalization for a medical exacerbation, etc. Moreover, the system may prompt members of the care management team (e.g., in the form of a task assignment) when ad-hoc activities should be performed (e.g., "Visit Mr. Jones by end of business on Jan. 21, 2014 and perform a care transition assessment").

Unannounced home visits are visits by the care management team designed to confirm that the caregiver is performing the requisite tasks based on the instructions from the care management system, and to ensure that core requirements are being satisfied. The care management system may include a module or algorithm that creates a task for the care management team to perform an unannounced home visit on a random basis over a certain period of time (e.g., creating a random event to perform an unannounced visit once per year, or on an interval as determined by regulatory or best practice requirements).

The care management step 150 may further involve the care management system calculating, updating, displaying, and creating tasks based on risk scores calculated for each individual client. This allows "at risk" indicators to be reviewed on both a regular and an ad hoc basis.

For example, the care management system may calculate risk scores, as described in more detail with respect to the risk analyzer and question library, below. The care management system may display the risk scores to indicate the extent of a calculated risk, and may indicate whether risk scores are changing over a predetermined period of time using a graphical or textual indication (e.g., displaying an arrow in the direction of movement of the risk scores, changing a color of the graphical display of the risk score corresponding to the direction of movement, etc.).

Upon receiving a selection of a risk score for a particular domain, the care management system may drill down into the domain and display risk scores for various subdomains encompassed by the domain. For example, a user may select the "functional" domain, and in response the system may display risk scores for subdomains of the functional domain, such as the risk of falling. This may allow members of the care management team to visualize and understand which factors are driving a change in the cumulative risk score for the domain.

Based on the calculated risk score and/or movement in the risk score over a predetermined time period, the risk score may recommend adjustments to the client's care. The risk analyzer may recommend an adjustment if the overall risk score, or the risk score for a particular domain or subdomain, rises above a predetermined threshold or changes at more than a predetermined rate.

Such adjustments may involve selecting new questions from a question library in order to supplement or replace the questions asked during a regular care giver interview. For example, questions targeted to identifying a client's risk of falling might be added to one or more subsequent care giver interviews in response to an increase in the client's falls risk score.

Such adjustments may also involve recommending an intervention. An intervention may include making a short-term or a long-term change in the care plan of the client, such as adding a new action to be performed on an individual or recurring basis. For example, the care management system might recommend that a patient see a particular specialist in response to a change in the medical domain's risk score, or might recommend ongoing visits by a therapist in response to a change in the psychosocial domain's risk score.

The care management system may include a library of interventions indexed according to particular risk factors or conditions. The interventions may be stored in a data structure that includes, for example, the name of the intervention, triggering factors or conditions that may be alleviated by the intervention, and may further include success rates for the intervention (which themselves may be indexed based on conditions that may improve or detract from the success rate). If a plurality of interventions are associated with a particular alleviated condition, the interventions may be ranked based on estimated success rate (accounting for client-specific conditions), and displayed for consideration by the care management team. Alternatively or in addition, one or more most-likely-successful interventions may be automatically selected by the care management system, based on an analysis of individual client risk factors, and displayed for consideration by the care management team.

Such adjustments may also involve the risk analyzer prompting (or creating an event, reminder, or to-do) for an at-risk case conference among the care management team. The case conference may be scheduled by the care management system based on individual risk factors and/or combinations of risk factors. The case conference may be scheduled in response to a risk score exceeding a predetermined threshold or changing at more than a predetermined rate. Alternatively or in addition, the case conference may be scheduled in response to a plurality of risk scores exceeding a cumulative threshold or changing at more than a predetermined cumulative rate. Thus, even if individual risk scores might not, by themselves, prompt the scheduling of an at-risk case conference, a combination of risk scores considered together may do so.

The predetermined threshold and/or the predetermined rate may be set on an individual basis based on known client information and/or risk factors. For example, the care management system may identify that patient has diabetes and congestive heart failure, and has been recently hospitalized.

The care management system may recommend that an at-risk conference be conducted in order to review possible interventions that might decrease the risk of re-hospitalization. The care management system may generate a list of possible interventions retrieved from the intervention library and may present recommended interventions at the at-risk conference. For example, proposed interventions may be included in a meeting invite generated by the care management system for the proposed at-risk conference.

The care management step 150 may further involve monitoring and reporting on incidents, tracking program interruptions, tracking care team and provider changes, and managing regulatory compliance.

Incidents may include events which have a negative impact on the health or well-being of the client, or which may indicate a risk for a future negative impact on the client's health or well-being. Incidents may include, for example, everything from a non-injurious fall to hospitalization for end-of-life care. The care management system may capture and store information related to incidents (e.g., through routine or ad hoc questions administered during care giver or care team interviews) based on automatic rules. The care management system may identify incidents that need to be reported to authorities by comparing the captured incident information to a regulatory or other database. The care management system may generate alerts, to-do items, or schedule events for reporting identified incidents to the appropriate authorities, and/or may report identified incidents automatically.

Program interruptions may include any circumstances which take the client outside of the at-home managed care environment. Program interruptions may include, for example, hospitalizations, suspensions from the program, temporary leave from the program due to medical problems, etc. Data on program interruptions may be captured by the care management system during regular interviews of the care giver and/or care management team. Data related to program interruptions may be used by the risk analyzer, and may be given increased weight when determining risks relating to increased program cost (as program interruptions are often a significant indicator of a risk of increased cost). Program interruptions may also need to be reported for regulatory or compliance reasons, and may be flagged and reported as described above for incidents.

The care management system may also track care team and provider changes. Care team and provider changes may involve the addition of a new care team member or provider, removal of an old care team member or provider, or the updating of credentials relating to the care giver or provider.

In some embodiments, the care management system may maintain or have access to a list of care givers or providers maintained separately from the data relating to the client. Each care giver or provider may be associated with information pertinent to the care giver or provider, such as contact information, credential information, etc. In some embodiments, each care giver or provider may be represented by an entry in a database, or by an object in an object-oriented environment. The care giver or provider may be associated with a particular client by generating a logical link, such as a pointer, URL, or other connection, from the care giver or provider information to the client data. The logical link may be stored with the client data, or may be stored with the care giver or provider information.

During the care management step 150, the care management system may track complaints and grievances, which in some embodiments may be entered by the care giver and automatically reported by the care management system to a compliance office.

The care management system may further be programmed with one or more rules for performing regular and routine administrative functions, such as regularly prompting for updated release forms, automatically auditing for compliance with best practice expectations and regulatory requirements (e.g., maintaining key forms in an up-to-date manner and ensuring that key tasks are performed in a timely manner) at predetermined intervals, updating emergency information, and screening caregivers.

During the care management step 150, the care management system may further provide educational materials for the caregiver and/or client. The care management system may retrieve or download educational materials relating to the care management system, the client's care, conditions that the client is known to have or be at risk for, and/or regulatory information from local or remote storage and display the educational materials for the client and/or caregiver.

Still further, during the care management step 150, the care management system may provide community providers, such as the client's PCP, with regular (e.g., semi-annual) updates on the client's care and condition. The system may prompt a member of the care management team, such as a registered nurse, to identify information stored in the care management system and may generate a report based on the identified information. Alternatively or in addition, the care management system may be preprogrammed with certain key domains, sub-domains, or indicators (e.g., current medications, functional status, incidents in the past 6 months, etc.) and may automatically generate and transmit a community provider report at predetermined intervals.

Thus, throughout the care management step 150, the client may be regularly evaluated in order to determine whether risk has been properly assessed and the right care plan has been created and implemented. In some circumstances, the client's care management may be ongoing for the rest of the client's life, and hence the client is unlikely to be discharged from the program. In other circumstances, the client's condition may improve to the point where the client is ready to be removed from active care under the program, or may deteriorate to the point where it is necessary to move the client to a more actively-managed care situation.

Accordingly, at step 160 the client may be discharged from the program. A determination as to whether the client may be discharged from the program may be made on a case-by-case basis, depending on the client's condition and the probability of client improvement or continued health if the client is left in or discharged from the program.

In some circumstances, it may be determined that the client's condition has deteriorated, or that the client has otherwise become unsuitable for the program. In these situations, the client may be discharged to a hospital, or managed care in a dedicated managed care facility may be recommended for the client.

The reason for the discharge may be documented in the care management system and may be stored as key outcome data for the risk analyzer. If the client is latter readmitted to the care management system, the reason for discharge may be given increased weight in determining future risk scores for the client. Further, in some embodiments the reason for discharge may be used to evaluate the care management system overall, so that changes may be made to the care management system for the benefit of other clients.

Following the discharge step 160, a follow-up check on the client may be performed (e.g., one month after discharge). Additional data may be identified during the follow-up visit and stored in the care management system. The additional data may be used to improve the care management system for the benefit of other clients.

The exemplary workflow described above provides an overall framework for evaluating whether a client is suitable for the program, populating the care management system with initial information, updating the information throughout the course of the client's care, and determining when additional action may be necessary by the care management team.

Each workflow step may be tightly integrated with the risk analyzer. At each workflow step, assessments may be started/updated and stored as versions in a data storage mechanism (described in more detail below with respect to FIG. 2). This process is called a "rolling assessment" whereby values from prior assessments are brought forward to current assessments for updating. This process may result in improved efficiencies wherein providers can quickly confirm existing values, add new ones, or broaden an assessment with other data points. The risk analyzer may incorporate changed and new values into increasingly refined intelligence (prompts, cues, content, workflows, etc.) presented to the users.

At various steps of the exemplary workflow, various actors may interact with a care management system. An exemplary care management system is described in detail below.

Care Management System

Figure 2:
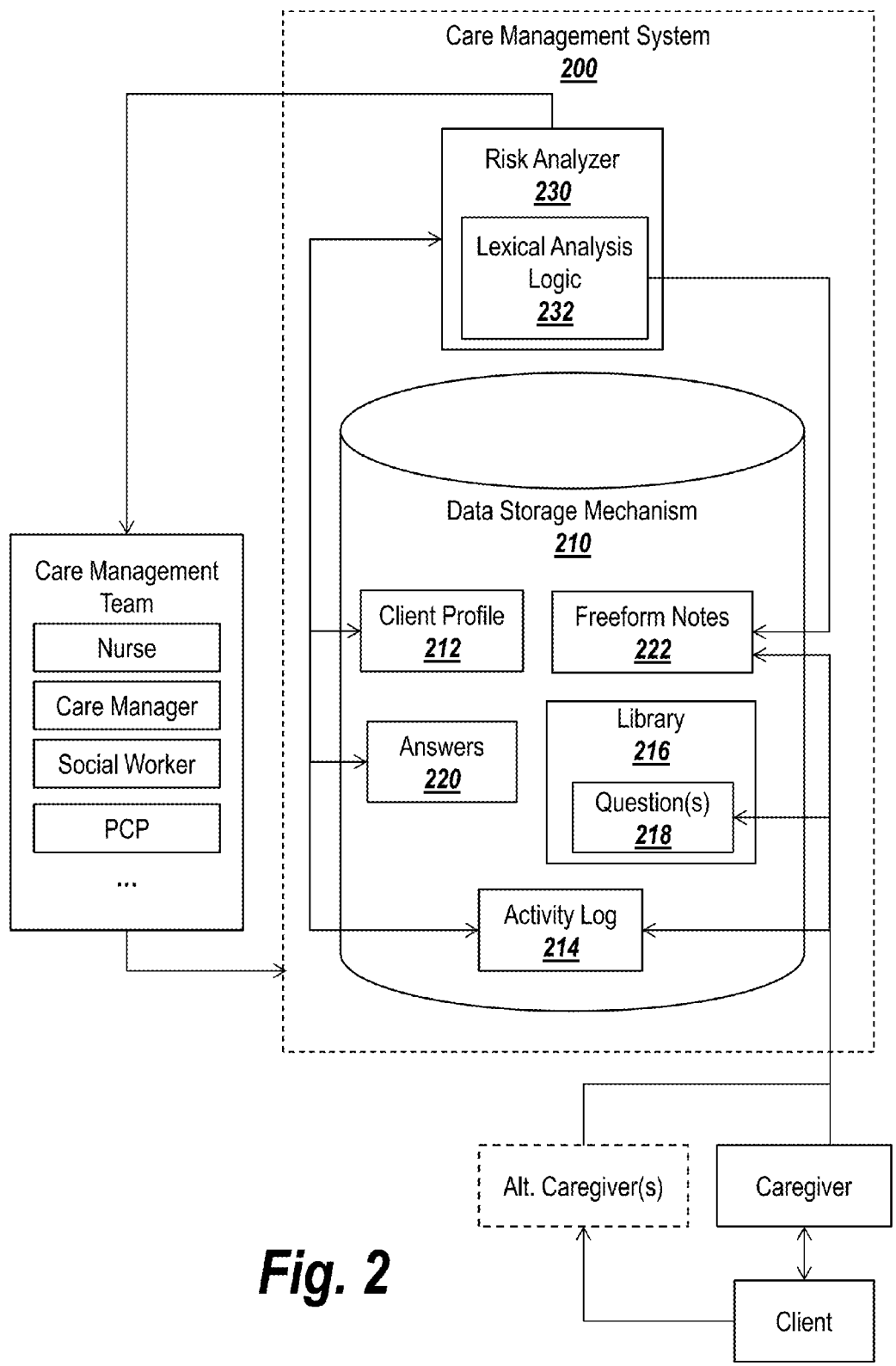
FIG. 2 is a block diagram depicting an exemplary care management system and interactions with the system by a care management team and caregiver.

FIG. 2 depicts an exemplary care management system 200. The care management system 200 may include, among other features, a data storage/entry mechanism 210 and a risk analyzer. Each of these features is discussed in more detail below.

Data Storage Mechanism

The care management system 200 may include a data storage mechanism 210 such as a database or other suitable data storage structure. The data storage mechanism 210 may store information relating to the daily activities, care, and condition of the client.

The data storage mechanism may store a client profile 212. The client profile 212 may include basic information about the client, such as name, address, age, and information concerning relationships associated with the patient (e.g., information related to the caregiver and/or the care management team).

The client may interact with the caregiver on a regular (e.g., daily) basis. The caregiver may then interact with the data storage mechanism 210 in order to record information relating to the daily activities and/or condition of the client. For example, the caregiver may be presented with a daily activity log 214, in which the caregiver may record the activities of the client. Activities may include any activity that may be relevant to the domains and sub-domains tracked by the care management system 200. The activity log 214 may include a predetermined list of activities for which data is requested.

The data storage mechanism 210 may further include a library 216, which may be (for example) a database containing input data for the care management system 200. For example, the library 216 may include a list of questions 218 to be posed to the caregiver during regular caregiver interview. The questions 218 may also include questions for the care management team to be answered during visits by the care management team to the client. The data storage mechanism 210 may further store the answers 220 to the questions 218, as retrieved from the caregiver through prompts by the care management system 200 during the caregiver interviews.

In addition to providing answers 220 to the questions 218, the caregiver may be given the opportunity to add freeform notes 222 at any time, including during a regular interview. The caregiver may be given the opportunity to add general notes, and/or may be presented with interface options for adding quick notes when answering specific questions 218. The quick notes may include notes related to the questions 218 and may be of particular relevance when determining a risk score for the domain/subdomain of the question 218.

The answers 220 to the questions 218 may be retrieved by a risk analyzer 230 and analyzed to calculate risk scores across the different domains of the questions 218 for the client. The risk analyzer 230 may consider the answers 220 to the questions in calculating the risk scores, and may further consider known information about the client as retrieved from the client profile 212. Furthermore, the risk analyzer 230 may use lexical analysis logic 232 to mine the freeform notes 222 for information that may affect the risk score.

According to one embodiment, the risk analyzer 230 may use the client profile 212, the answers 220, and the freeform notes 222 together in order to calculate the risk score. Alternatively or in addition, the risk analyzer 230 may calculate an initial risk score based on the client profile 212 and the answers 220, and may refine the risk score based on the freeform notes 222. Such an embodiment may be useful in terms of processing efficiency, since the client profile 212 and answers 220 may be in the form of "structured" data which can be quickly and quantitatively assessed, whereas the freeform notes 222 may be in the form of "unstructured" data which is qualitative in nature and requires more processing in order to extract relevant information. In some embodiments, the lexical analysis logic 232 may analyze the freeform notes 222 only if the initial calculation of the risk score yields an ambiguous result (e.g., the risk score is within a predefined tolerance of a threshold that would cause the risk score to rise or fall to a different value but does not exceed the threshold). Thus, the freeform notes 222 can be used by the care management system 200 to resolve ambiguous conditions.

By answering preselected questions at predetermined and/or triggered intervals, participating in the activity log, and entering freeform notes, the caregiver and care management team provide inputs to the risk analyzer 230 for use in calculating a risk score. Exemplary interfaces and data structures for providing such input data is described in detail below.

Input Data: Activity Log, Question Library and Interface, and Freeform Notes

Input for analysis by the risk analyzer 230 may come from a number of places, including pre-existing data and client profiles stored in local or remote storage, answers to questions from the question library 216, the activity log 214, and the freeform notes 222, among other possibilities. The question library 216, activity log 214, and freeform notes 222 are described in detail in this section.

The data storage mechanism of the care management system may store questions in a question library 216. The questions may be designed to probe particular aspects of the client and/or caregivers condition and activities.

The questions of the question library 216 may be of, for example, three different types. A first group may include Derived Questions, which are questions based upon known client conditions (e.g., captured from previous assessments such as the workflow described above. A second group may include Core Questions, which may be asked to all consumers and may be related to regulatory and/or best practice requirements. A third group may include Polling Questions that will be asked across a period of time to capture other information not captured by the first two groups of questions (e.g., customer satisfaction, burden, etc.).

Within the three different types of questions, there may be two sub-types: general questions and targeted questions. General questions regarding the client and/or caregiver may be concerned with the overall health or satisfaction of the client and/or caregiver, rather than any particular or specific condition. Targeted questions may be directed to evaluating particular conditions of the client. For example, the library may include questions designed to detect depression or anxiety. These targeted questions may be selected or derived from a client profile as determined during the referral, intake, and assessment steps of the workflow.

General questions may be mixed with targeted questions on a particular day, or the system may alternate when each type of question is presented. For example, on Day 1 the system may present the caregiver with 50 general questions about the client, while on Day 2 the system may present the caregiver with 15 targeted questions.

For either general questions or targeted questions, a given answer may trigger further follow-up questions if the answer suggests that a particular condition may be present. For example, if a general question about the client's daily activities indicates a risk of depression, the system may follow-up the general question with a series of specific questions designed to further probe for indicators of depression.

In one embodiment of triggering questions, questions in the question library 216 may be stored as structured data sets including a question and a plurality of possible answers. Certain possible answers may be flagged as trigger answers, which are stored with a link to (or identifier of) another question that is triggered as a result of receiving the trigger answer. The triggered questions may be posed immediately, or over a period of time during which the risk analyzer estimates (based on statistical data, models, preprogrammed information, etc.) that the client is at increased risk for a condition associated with the triggering question. In some embodiments, a combination of answers may be used to trigger other questions. For example, a client whose recent answers indicate an increased risk for falls might receive an increased number of falls-related questions during a time frame in which the risk analyzer evaluates that the client is at the increased risk for falls.

The questions may also include regulatory questions designed to evaluate the program or care management system itself. Questions directed to the caregiver or to regulatory requirements may be asked less frequently than questions designed to evaluate the client's status (e.g., caregiver or regulatory questions may be asked every six months, while client questions are asked on a daily basis).

Some questions may accept a number or a simple yes/no answer. Other questions may allow for freeform answers and/or the addition of clarifying "quick notes," which may be evaluated in a manner similar to the caregiver's freeform notes (described below)

The questions may be asked iteratively and/or on a rolling basis. Thus, as more time passes during the client's participation in the program, the care management system's understanding of the client's condition and/or needs grows in depth. Furthermore, as the care management system gathers more information relating to the client's status, the care management system may select more relevant questions, allowing for a specialized and especially relevant profile of the client to be generated.

In one embodiment of questions asked on a rolling basis, a subset of questions from the question library 216 may be selected by the care management system 216 for presentation during a caregiver assessment or interview. The order and frequency at which particular questions are selected from the question library may be determined by the risk analyzer based on known information about the individual client and/or a prediction by the risk analyzer as to the frequency at which the answers to certain questions may change. For example, some questions may be posed on a regular basis depending on how quickly the risk analyzer predicts the answers may change (e.g., asking questions pertaining to the client's ability to perform housework on a weekly basis, versus asking questions pertaining to the client's ability to eat on a daily basis). Known information about the client may prompt the risk analyzer to pose certain questions on a more frequent basis than the risk analyzer otherwise would. For example, a client whose profile information, such as age, indicates an increased risk of incurring an injurious fall may receive more falls-related questions than a client whose profile information does not indicate an increased risk of incurring an injurious fall.

The answers to some questions (e.g., gender, height, etc.) may be unlikely to change much, or at all, during the care management process. Accordingly, questions relating to these attributes may be posed on a very infrequent basis, or may never be posed and instead the care management system may rely on the caregiver or a member of the care management team to manually update the attribute (e.g., during a yearly review).

The answers to some questions (e.g., age) may be derivable from existing information (e.g., birth date) without the need to pose the question to the caregiver or client. In exemplary embodiments, the care management system may update such information on a regular basis (e.g., monthly), on an as-needed basis (e.g., when such information is called for by the risk analyzer), and/or in response to the occurrence of an event (e.g., on the client's birthday).

Thus, the care management system provides a detailed record of the status of the client. Because the care management system directs the caregiver's data entry activities through the use of questions and the activity log, it is not necessary for the caregiver to determine what information may be relevant to the care of the client. Accordingly, the caregiver does not need to filter information that is deemed to be irrelevant (but which may be relevant), and it is more likely that relevant information will be noted. Similarly, if data is initially ignored as irrelevant but determined to be relevant at a later time, the data is persistently recorded so that the care management team can review it (e.g., to notice when or if a trend began).

Figure 3:
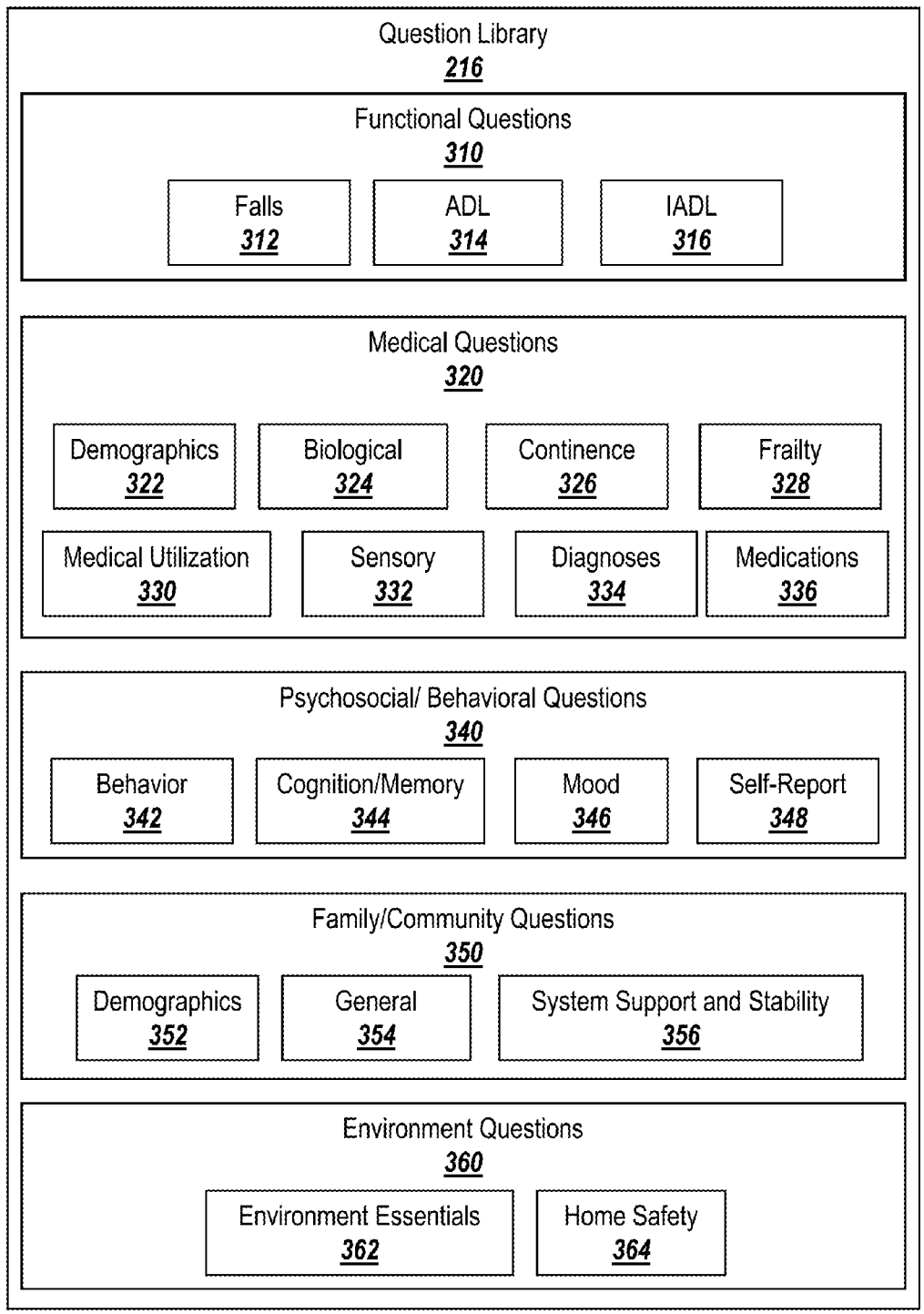
FIG. 3 is an exemplary question library and list of domains/subdomains according to an exemplary embodiment.

FIG. 3 depicts an exemplary question library 216. The question library includes questions related to numerous activities, grouped into one or more domains. The questions of the question library 216 may be organized into domains and subdomains. A domain is a category of related parameters that describe an aspect of the client's condition. For example, activities may be grouped into the "functional" domain, which describes the mechanical actions taken by the client throughout the day (e.g., bathing, eating, dressing, etc.). The specific actions within the domain (e.g., bathing, eating, dressing, etc) are referred to herein as "sub-domains." Some questions (e.g., age, gender, etc.) may pertain to more than one domain or subdomain.

Other domains may include, but are not limited to, medical, psychological/behavioral, family/community-related, and environmental. One of ordinary skill in the art will recognize that more or fewer domains may be used, depending on the specific conditions to be evaluated for a particular client.

In evaluating activities within domains and sub-domains, a "scale" may be used for quantifying the activity (for example, noting the level of assistance required for the activity). Scales may vary by activity, and may be selected according to regulatory, best-practice, and/or industry standard considerations.

The exemplary question library 216 includes a set of questions in the functional domain 310. As noted above, the functional domain may describe mechanical actions taken by the client, which may be performed on a daily basis (or more or less frequently).

For example, the set of functional questions 310 may include questions relating to a client's risk of incurring a fall 312. The falls questions 312 may be associated with a fall risk scale, and may be obtained according to (in one embodiment) the QuickScreen falls risk assessment.

The set of functional questions 310 may further include questions related to Activities of Daily Living (ADLs) 314. Activities of Daily living may include daily self care activities performed on behalf of the client, with or without supervision or help, on a daily basis. The ability or inability to perform ADLs may provide a measurement of the client's functional status and ability to care for themselves. Activities of daily living include, but are not limited to, dressing, bathing, eating, walking, toileting, and hygiene.

The ADL questions 214 may include questions to determine a count of ADLs performed on a given day, a level of assistance provided by the caregiver for the client for the ADLS, and/or a hierarchy of the ADLs (such as a hierarchy according to the interRAI scale of the interRAI organization).

The set of functional questions 310 may further include questions related to Instrumental Activities of Daily Living (IADL) 316. IADLs are similar to ADLs in that they represent daily activities that may be performed by a client. However, whereas ADLs are typically required to fundamental functioning, IADLs generally relate to the ability of a client to live independently. IADLs may include, but are not limited to, performing housework, taking medications, managing money, shopping, communicating, and using transportation. The IADL questions 316 may be scaled based on the interRAI Clinical Assessment Protocol (CAP).

The question library 216 may further include a set of medical questions 320. Medical questions 320 may pertain to the health of the client, including questions about diseases, diagnoses, medications, injuries, etc.

The medical questions 320 may include demographic questions 322, such as age, gender, marital status, and race/ethnicity. Answers to demographic questions may be entered into the care management system during the initial intake and/or assessment process, upon a change to a demographic attribute (e.g., marriage), and/or in response to questions posed during a caregiver assessment or interview.

The medical questions 320 may further include biological questions 324 relating to the client's height and weight. The biological questions may be evaluated, for example, by a registered nurse during one of the nurse's scheduled home visit.

The medical questions 320 may further include questions related to continence 326, such as bladder and bowel functionality.

The medical questions 320 may further include questions related to the client's frailty. Several frailty evaluation standards exist and are suitable for use with the present invention, such as the Cumulative Illness Scale and the CGH Frailty Index.

The medical questions 320 may include questions related to medical utilization 330. For example, an interface of the care management system 200 may present a list of key medical events, such as ER visits without hospitalization, urgent care visits, physician visits by a primary care provider (PCP), physician visits by other physicians, ambulance rides, and hospitalizations. Each key medical event in the list may be associated with a counter or other indicator that represents the number of times the associated key medical event occurred during the period under review. In some embodiments, the counter may be selected directly and altered using (for example) a numerical input from a keyboard. Alternatively or in addition, the counter may be altered using physical or software buttons for increasing or decreasing the counter to the correct counter value.

The medical questions 320 may further include questions related to the client's sensory capabilities 332. The sensory questions 332 may include, for example, questions relating to the client's hearing and vision. The sensory questions 332 may include questions relating to objective tests, such as the client's performance on an eye test performed by an optometrist or a hearing test, and/or may include subjective questions such as the caregiver's perception of the client's sensory capabilities.

The medical questions 320 may include questions related to diagnoses 334 of the patient. For example, an interface of the care management system 200 may present the user with a list of current diagnoses, which may be organized using an identifier such as a name or medical code (e.g., the ICD-9 Code), and may be presented with a description. A "no change" indicator may be presented, which may be selected by the caregiver if there have been no changes to the client's existing diagnoses. A "remove" indicator may be associated with each diagnosis and may be displayed in close proximity to the associated diagnosis. Upon receiving a selection of a remove indicator associated with a diagnosis (e.g., indicating that the diagnosis is no longer valid), the diagnosis may be removed. Further, an "add" indicator may be provided. In response to receiving a selection of the add indicator, the system may display a diagnosis entry interface that allows diagnoses to be entered using the above-noted identifiers. Alternatively or in addition, the diagnoses may be selected from a list of descriptions.

Similarly, the set of medical questions 320 may include questions regarding medications 336. Questions regarding medications 336 may include questions relating to high risk medications based on a list of medications (e.g., Beer's List), a count of all the client's current medications, and a list of the client's psychotropic medications.

The questions regarding medications may be presented through an interface of the care management system 200. The interface may present a list of known medications 336 that the client is using. The medications may be organized by an identifier such as a medication name or identification number. Each medication may be associated with a base dose amount, a number of doses to be taken by the client, the form of the dosage, and the frequency of the dosage. An "information" indicator may optionally be provided. Upon receiving a selection of the information indicator, the system may present additional information, such as a narrative description of the medication, a list of conditions to be treated by the medication, and common items (e.g., food or other medications) that may interact with the selected medication.

Furthermore, one or more warning indicators may be displayed in close proximity to a medication. The warning indicators may be used to inform the caregiver that the client's use particular medication should be reviewed or discussed with a medical expert (e.g., due to a change in circumstances, a particular medication may need to be reconsidered) or that some action should be taken with respect to a medication (e.g., indicating that it is nearing time to refill a given medication).

A "no change" indicator may also be presented, which may be selected by the caregiver if there have been no changes to the client's existing medications. A "remove" indicator may be associated with each medication and may be displayed in close proximity to the associated medication. Upon receiving a selection of a remove indicator associated with a medication (e.g., indicating that the client is no longer taking the medication), the selected medication may be removed. Further, an "add" indicator may be provided. In response to receiving a selection of the add indicator, the system may display a medication entry interface that allows medications to be entered using the above-noted identifiers. Alternatively or in addition, the medication may be selected from a list of descriptions.

The question library 216 may include questions relating to psychosocial and/or behavioral issues 340. Psychosocial and behavioral issues may generally relate to the clients neurological status, mental state, and sociability.

The set of psychosocial/behavioral questions 340 may include questions related to behavior 342. Behavioral questions 342 may include questions relating to alcohol use or abuse by the client (e.g., based on the CAGE Scale), behavior problems (e.g., based on the interRAI CAP), non-adherence to the care management system's requirements or instructions from the caregiver and non-adherence to a medication schedule (e.g., based on the CGH Scale), and/or social isolation (e.g., based on the interRAI specifications for social isolation).

The psychosocial/behavioral questions 340 may further include questions relating to the client's cognition/memory 344. Such questions may include questions related to the client's cognitive decision making, cognitive condition (improving or worsening), procedural memory, and short-term memory. Each of these items may be evaluated, for example, based on the interRAI specifications for cognition and memory.

The psychosocial/behavioral questions 340 may further include questions relating to the client's mood 346, such as questions evaluating depression or anxiety (e.g., based on the interRAI CAP).

The psychosocial/behavioral questions 340 may further include questions allowing the client to self-report certain aspects of the client's status or care 348. Self-report questions 348 may include questions regarding how the client perceives their health status and the client's belief system regarding health care in general.

The question library 216 may further include a set of questions relating to the client's family and community 350. Family and community questions 350 may relate to the client's social environment and relationships.

The set of family/community questions 350 may include questions relating to demographics, 352. Such questions may include the client's age, gender, and marital status.

General family/community questions 354 may include the client's self-reported health status, health literacy (e.g., based on the CGH Health Literacy Screen), health care beliefs, and whether the client is experiencing a language barrier (e.g., based on the CGH language barrier screen).

The set of family/community questions 350 may further include system support and stability questions 356. The system support and stability questions 356 may be questions targeted at the evaluating the client's support network. System support and stability questions 356 may include, for example, questions relating to abuse or neglect of the client (e.g., based on the CGH abuse-neglect warning signs), an emergency plan pertaining to the client (e.g., based on the CGH ACG scale), a sense of the strain or burden placed on the community and/or caregiver by the client (e.g., based on the CGH CG-Burden Ruler and/or the CGH Caregiver Strain Inventory), and the amount of care support needed for the client (e.g., based on the CGH CG-Support Ruler).

The question library 216 may further include a set of questions relating to the client's environment 360. The environment questions 360 may relate to the client's physical environment, such as the home in which the client is being cared for.

The set of environment questions 360 may include questions relating to environment essentials 362. Environment essential questions 362 may include questions relating to the client's home (e.g., based on the CGH Home Essentials Screen), the client's life requirements (e.g., based on the CGH Life Essentials Screen), and the client's security (e.g., based on the CGH Security Essentials Screen).

The set of environment questions 360 may further include questions relating the safety of the home in which the client is being cared for 364. Such questions may include a home safety screen, such as the CGH Home Safety Screen.

One of ordinary skill in the art will recognize that the question library 216 of FIG. 3 is exemplary, and that more or different questions, domains, subdomains, and scales may be present in the question library 216. Furthermore, the answers 220 may be structured in a manner similar to the question library 216. Thus, the exemplary question library 216 may serve as a structure for input information into the risk analyzer regardless of whether any actual questions are asked pertaining to one of the questions in the exemplary question library. For example, although demographics questions 322, 352 may be rarely (or never) asked, such demographic information may still reside in a database of answers 220 to be provided to the risk analyzer.

Figure 4B:
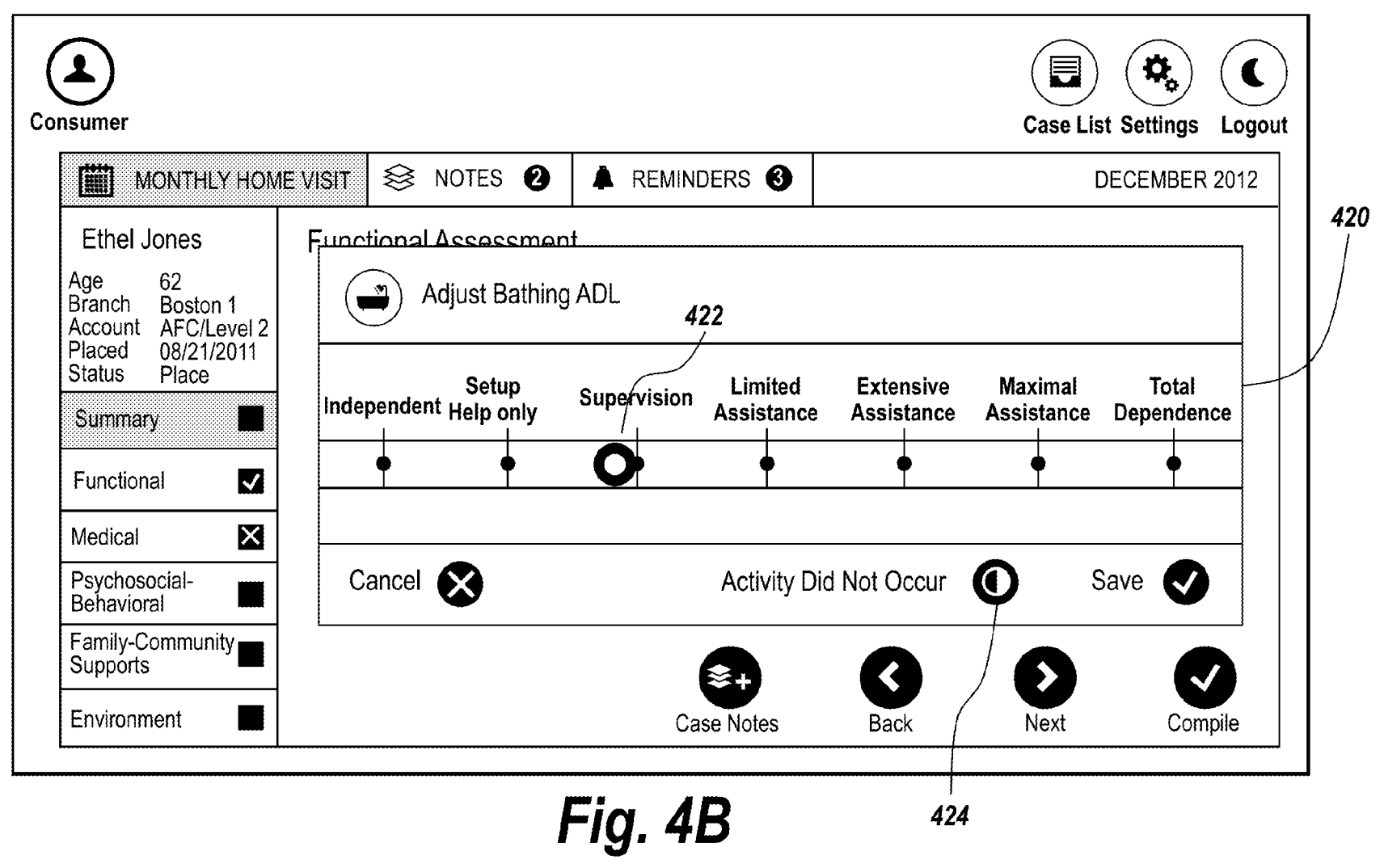

In addition to the questions from the question library, the care management system may accept input into the activity log. FIGS. 4A and 4B depict exemplary embodiments of interfaces for the care management system through which a caregiver can enter activities related to the "functional" domain.

Upon entering the activity log, the caregiver may be presented with an interface containing a list 410 of activities for which data is requested, as shown in FIG. 4A. The list 410 may be selected, for example, based on activities represented in the library of questions 216. In an exemplary embodiment, the list 410 may be selected based on ADLs 314 and IADLs 316 in the set of functional questions 310. Some or all of the ADLs 314 and IADLs 316 may be selected for evaluation on a given day, depending on whether the risk analyzer determines that a particular ADL 314 or IADL 316 should be evaluated on a given day.

In some embodiments, the list 410 may include all of the activities for which data is requested for a particular day (and may exclude any activities for which data is not requested). In other embodiments, the list 410 may be consistent from day-to-day, and may include an indicator 412 indicating that input is requested for a specified activity for a given day.

The caregiver may select an activity from the list 410 to provide detailed information. For example, the caregiver may select a "bathing" activity 414 in the interface to log the client's bathing activity for the day. In response to receiving a selection of the "bathing activity" in the interface, a new interface may be presented that is specific to the selected activity. An exemplary interface for the bathing activity is shown in FIG. 4B.

The selected activity may be associated with a scale 420 that indicates how much assistance the client required in performing that activity. An indicator or graphical element 422 may be provided for indicating on the scale 420 how much assistance the caregiver provided. Further, an indicator or graphical element 424 may be presented for indicating that the activity did not occur during the time frame in question.

The risk analyzer may analyze the number of activities entered in the activity log, the level of assistance required for each activity, and trends in the number of activities and assistance required in formulating a risk score for the domain encompassed by the activity (e.g., the functional domain, in the case of the bathing activity).

Figure 5B:
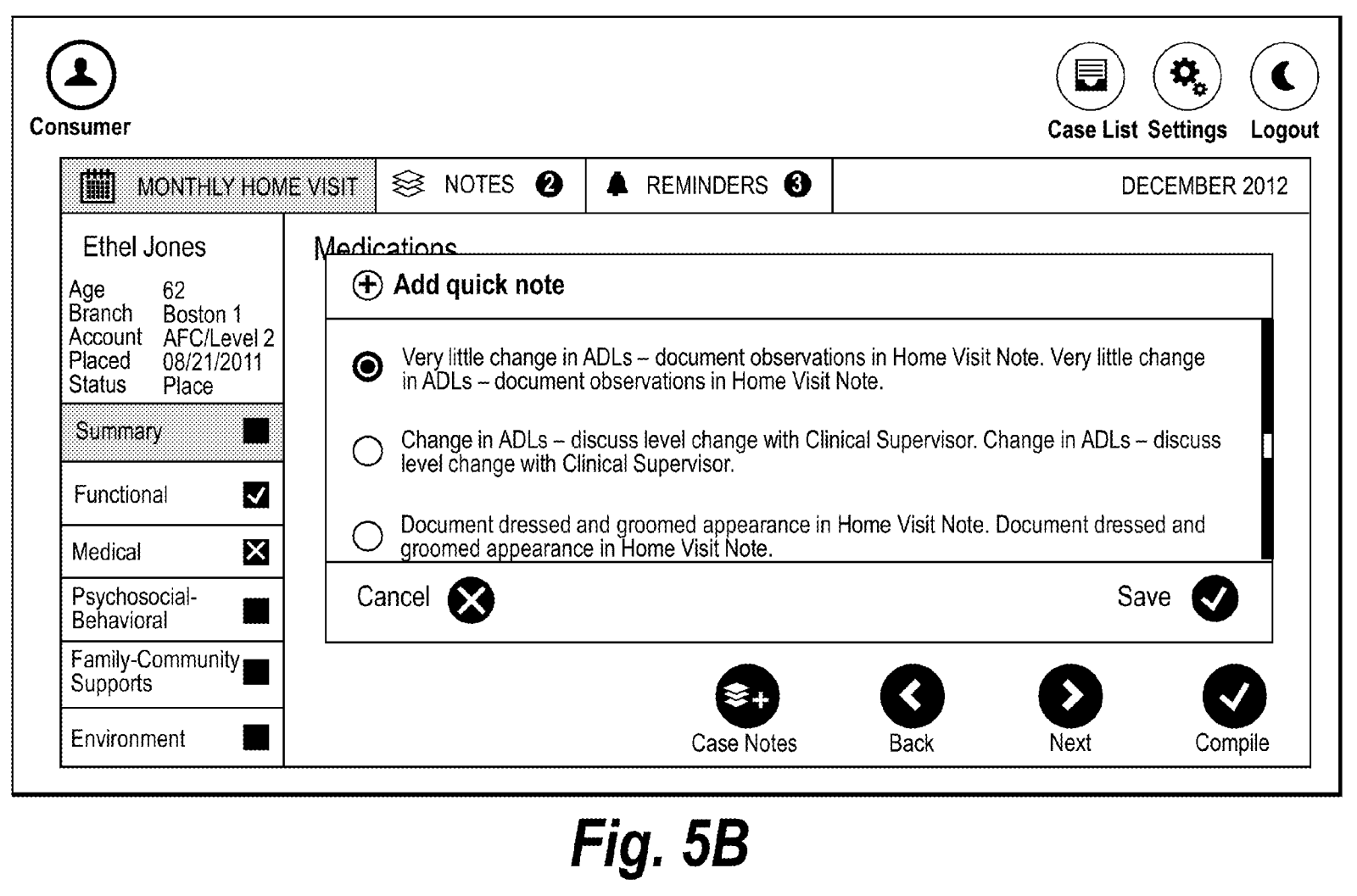

As shown in FIGS. 5A and 5B, in addition to the activity log and individually posed questions the caregiver may add freeform notes to the care management system. The freeform notes allow the caregiver to note anything that the caregiver deems to be of interest in the client's daily activities. In practice, it has been found that not all caregivers utilize the option of adding freeform notes. However, those who take the time to enter such freeform notes often provide particularly useful information. Accordingly, the information in the freeform notes may be separately analyzed in order to inform a risk assessment.

The freeform notes may be of a general nature, as shown in FIG. 5A. Freeform notes of a general nature may be entered at any time during or after an interview or assessment. The freeform notes may also be of a more specific nature, as shown in FIG. 5B. Such notes are referred to herein as quick notes. Quick notes may be entered in conjunction with a response to a specific question, in conjunction with a specific activity entered into the activity log, or in relation to a particular domain or subdomain.

Analysis of the freeform notes may be made by a lexical analyzer, as described in more detail in relation to the risk analyzer below.

The notes may be added, entered, or reviewed by the care management team. The care management system may present options to the care management team that allows team members them to "tag" specific notes. The tags may identify follow-up actions, may associate a specific note for further follow up, or may flag a particular item for a team review or case conference.

Thus, information may be entered into the system (among other possibilities) through answers to questions, the activity log, and/or in the form of freeform notes. An exemplary overall workflow for entering and analyzing such information is summarized in FIG. 5. The workflow of FIG. 5 may be applied to any individual in the program, such as the caregiver or a member of the care management team. Such an individual is referred to herein as a "contact."

First, the contact may log in to the system at step 610. As noted above, a different interface and set of questions may be provided to each contact depending on the contact's role. For example, if the contact is the caregiver, the contact may be presented with an interface like the one shown in FIG. 4A. Alternatively, if the contact is a nurse, the contact may be presented with an interface like the one shown in FIG. 8.

At step 612, the contact may be prompted to perform a task. In this context, a "task" involves answering questions or providing input as directed by an assessment, updating an activity log, or entering a freeform note.

At step 614, an assessment may be generated by the care management system based on the client's profile, previous responses to questions, and the questions available to the care management system in the library of questions. The contact may answer the questions in the assessment, which may prompt the risk analyzer to run a risk assessment at step 616. If the risk assessment determines that the contact's answers suggest a particular condition (e.g., depression), the system may trigger additional questions at steps 618-620 to further investigate the condition.

After the additional questions are answered by the contact (or by another contact), the system may automatically trigger an updated risk assessment at step 622. Alternatively, instead of automatically triggering a new risk assessment, the system may analyze some or all of the newly-answered questions to determine whether a new risk assessment is warranted.

If the contact chooses to add a freeform note at any point during the process (step 624), a lexical analysis may be performed at step 626 (lexical analysis is discussed in more detail below). Based on the lexical analysis and/or the risk assessment, recommendations for interventions may be determined (interventions are discussed in more detail below).

The contact may also choose to update the activity log(step 628). Based on the information entered into the activity log, processing may proceed to step 616 and the risk analyzer may run a risk assessment. Processing may then proceed to step 618, wherein it is determined whether the risk assessment as generated or updated with respect to the activity log warrants additional questions.

Figure 6:
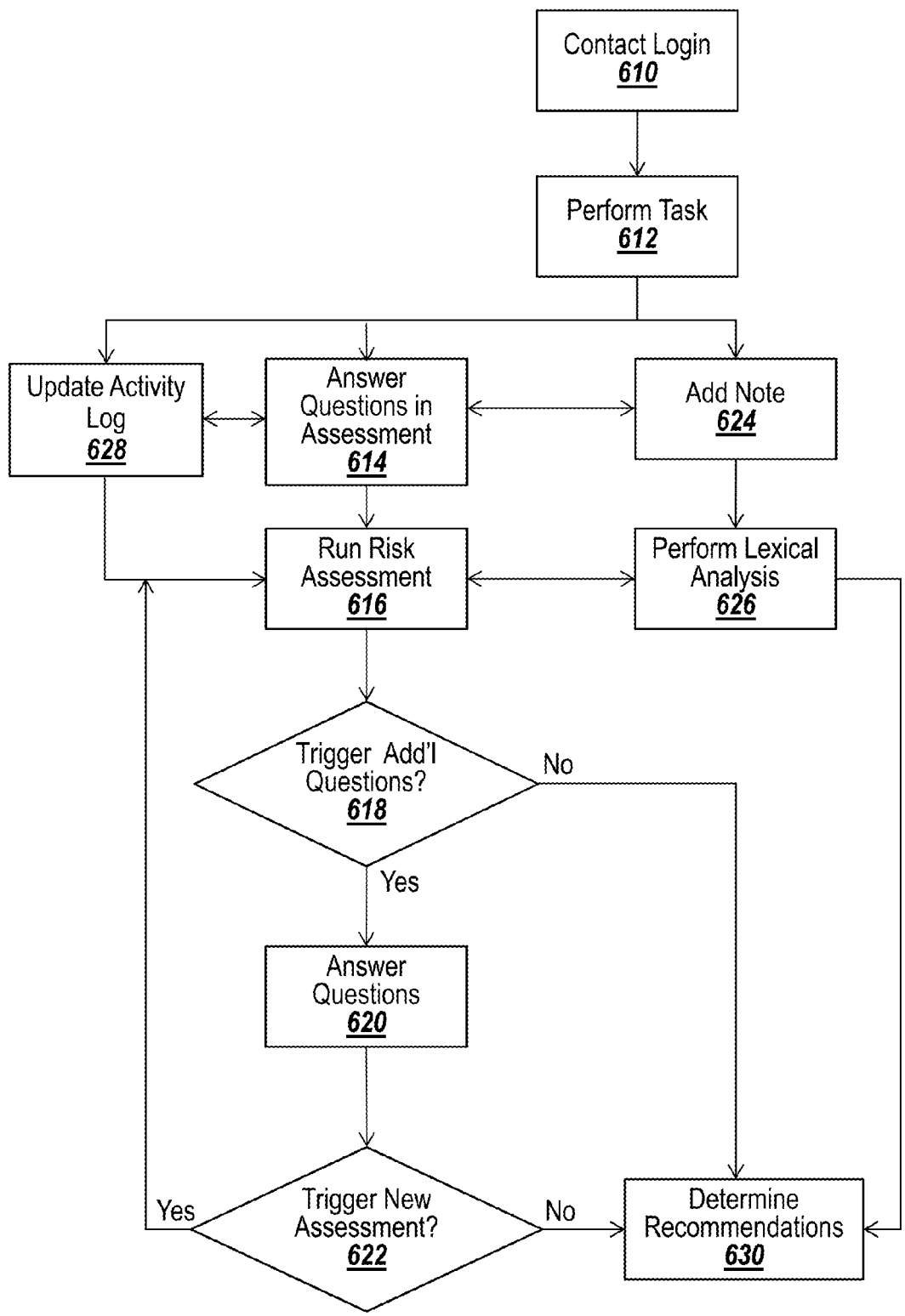
FIG. 6 is a flowchart depicting an exemplary workflow for providing information to the care management system.
Figure 7A:

Using the exemplary procedure described in FIG. 6, input data may be provided for the risk analyzer and a care plan may be created or updated. FIGS. 7A-7D depict exemplary interfaces suitable for one example of information entry into the care management system (specifically, information about the client's risk of a fall). FIGS. 7A-7B depict examples of multiple choice questions 710 having a limited number of possible structured answers 712. A selector 714 may be presented on the interface for selecting one of the possible structured answers 712.

The assessment may be divided into two or more steps or portions 716. Upon answering all of the questions posed during the assessment, the contact may select a selector 718 to indicate that this portion of the assessment is complete. The care management system may then move to the next step 716, as shown in FIG. 7C.

Figure 7C:

As shown in FIG. 7C, based on the answers provided in the question portion of the assessment, the risk analyzer may evaluate the client's chance of incurring a fall and, if a fall were to occur, the chance that the fall would be injurious. The care management system may display the results of the calculation on a matrix 718 in order to visualize the results.

Upon completing this step or portion, the contact may select another indicator 720 to indicate that the review of the assessment results is complete.

Figure 7D:
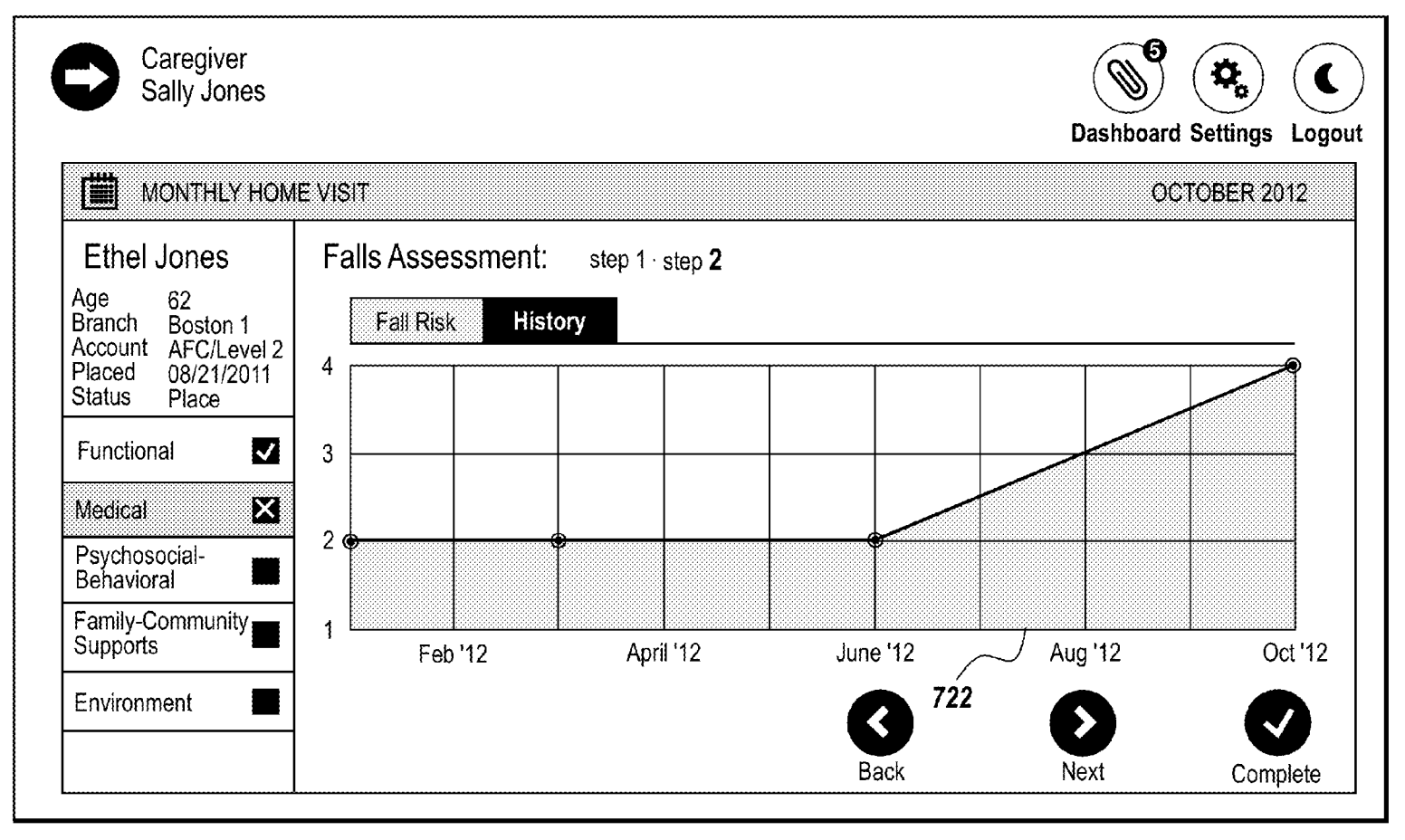

Optionally, the care management system may allow the contact to review historical answers to the questions in order to allow the contact to review trends in the client's care. For example, FIG. 7D depicts the historical answers to the question posed in FIG. 7C in the form of a graph 722.

Tailored Interfaces

As previously noted, different contacts interacting with the care management system 200 may be presented with different "tailored" interfaces depending upon the contact's responsibilities. Different contacts may be responsible, or primarily responsible for different domains of questions. For example, the caregiver may be primarily responsible for providing information about the functional domain, a registered nurse may be primarily responsible for providing information about the medical domain, a social worker may be primarily responsible for the psychosocial/behavioral domain (perhaps in conjunction with the caregiver), and the care manager may be primarily responsible for the environmental domain. The risk analyzer may provide each contact with questions from the contact's domain through the custom tailored interfaces.

As significant benefit of the presently described care management system is that information from multiple domains as provided by multiple individuals specialized to operate in those domains is aggregated and used holistically to evaluate the client's risk of negative outcomes.

Because the information may be analyzed in real time, the care management system allows potential problems across multiple domains to be discovered and addressed quickly, particularly in the case where a change in one domain affects another domain. For example, if a PCP prescribes a client a new pain medication (medical domain) and the client subsequently experiences a fall (functional domain), the care management system may flag the new medication as possibly contributing to a loss in balance or change in gait by the client. This may occur more quickly than if the client waited to describe their functional problems at a regular doctor's visit.

Furthermore, the client and/or PCP may not correlate the change in a functional attribute, such as balance and risk for falls, with a change in a medical attribute, such as a new medication. Thus, the care management system may identify items that could otherwise be overlooked by experts concentrating on individual domains.

Each tailored interface may include questions and logs relevant to the particular responsibilities of the individual care management team member (e.g., the nurse may be presented with interfaces allowing the nurse to enter medical information, while the social worker may be presented with interfaces allowing the social worker to enter behavioral or community-oriented information). Similarly, the care management team may add notes to the system in the same way as the caregiver may add notes.

For example, upon logging into the care management system 200, the caregiver may be presented with options for accessing a subset of the questions 218 in the library 216, as shown in FIGS. 4A-4B and 7A-7D. The caregiver may also be able to access the freeform notes 222 for which the caregiver is the author. The caregiver may be restricted from viewing questions 218 which are not currently awaiting answers, and freeform notes 222 for which the caregiver is not the author (e.g., notes from the client's nurse).

Figure 8:
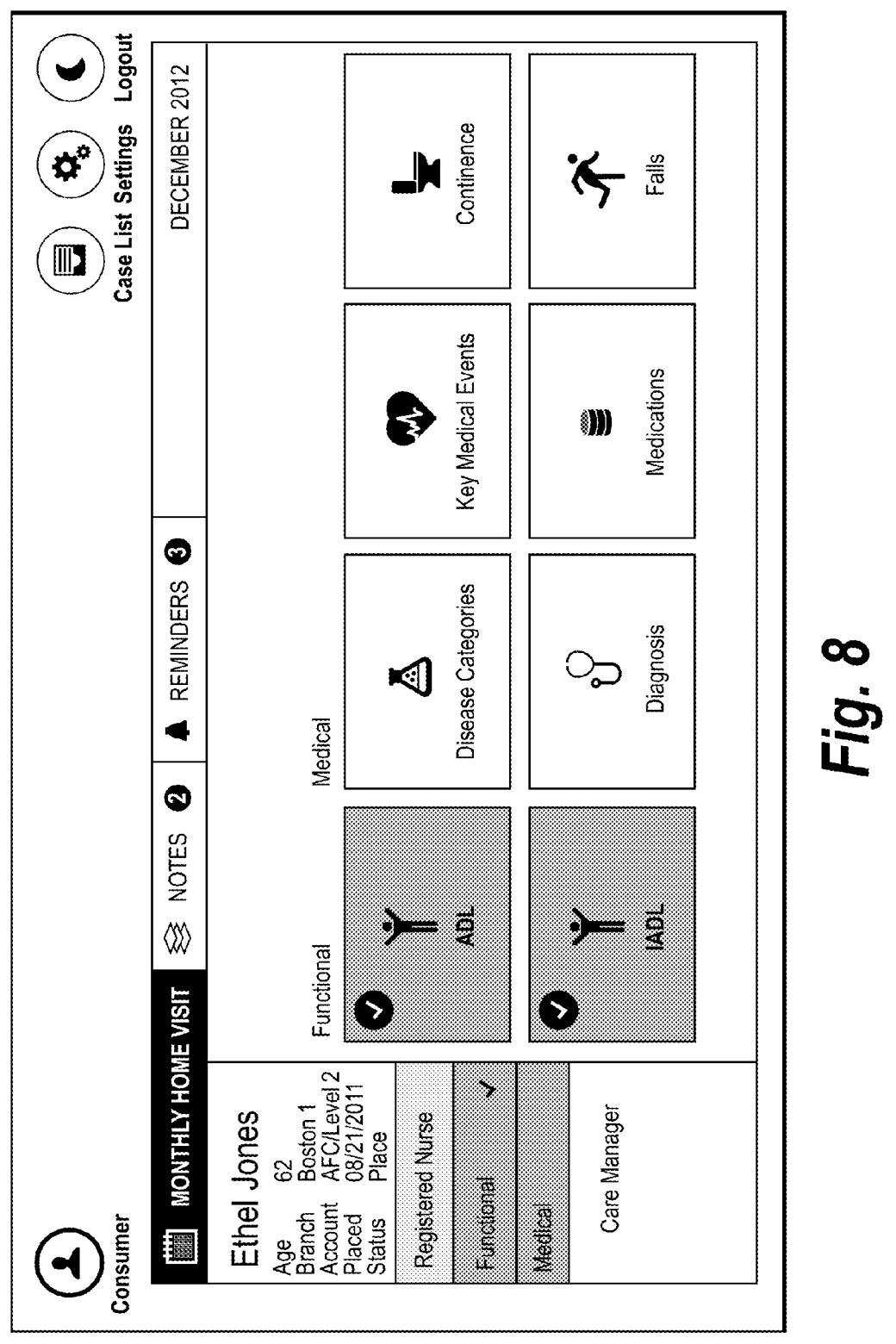
Figure 9A:
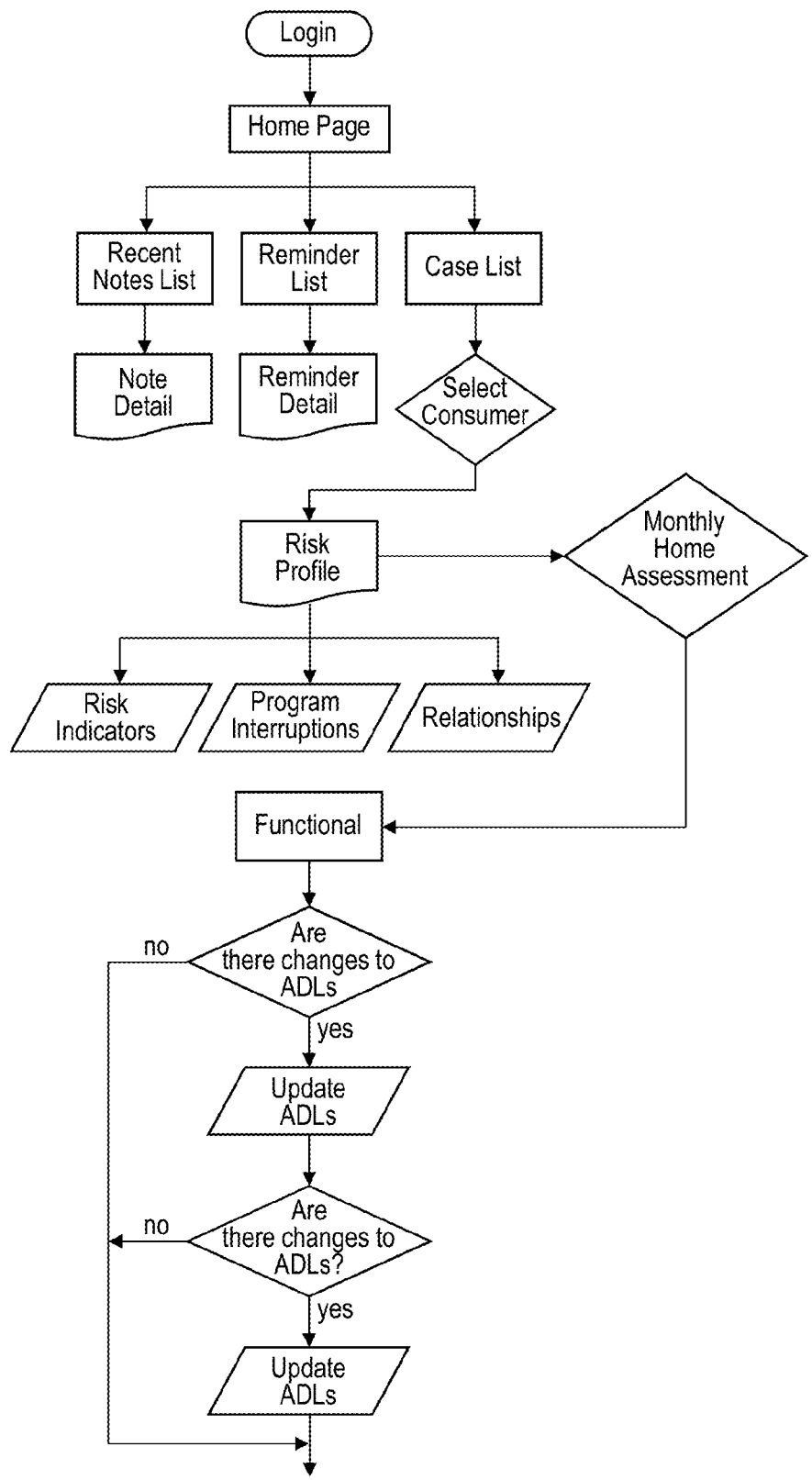
FIGS. 9A-9B depict a flowchart depicting interactions with the care management system by a registered nurse during a scheduled monthly visit.
Figure 9B:
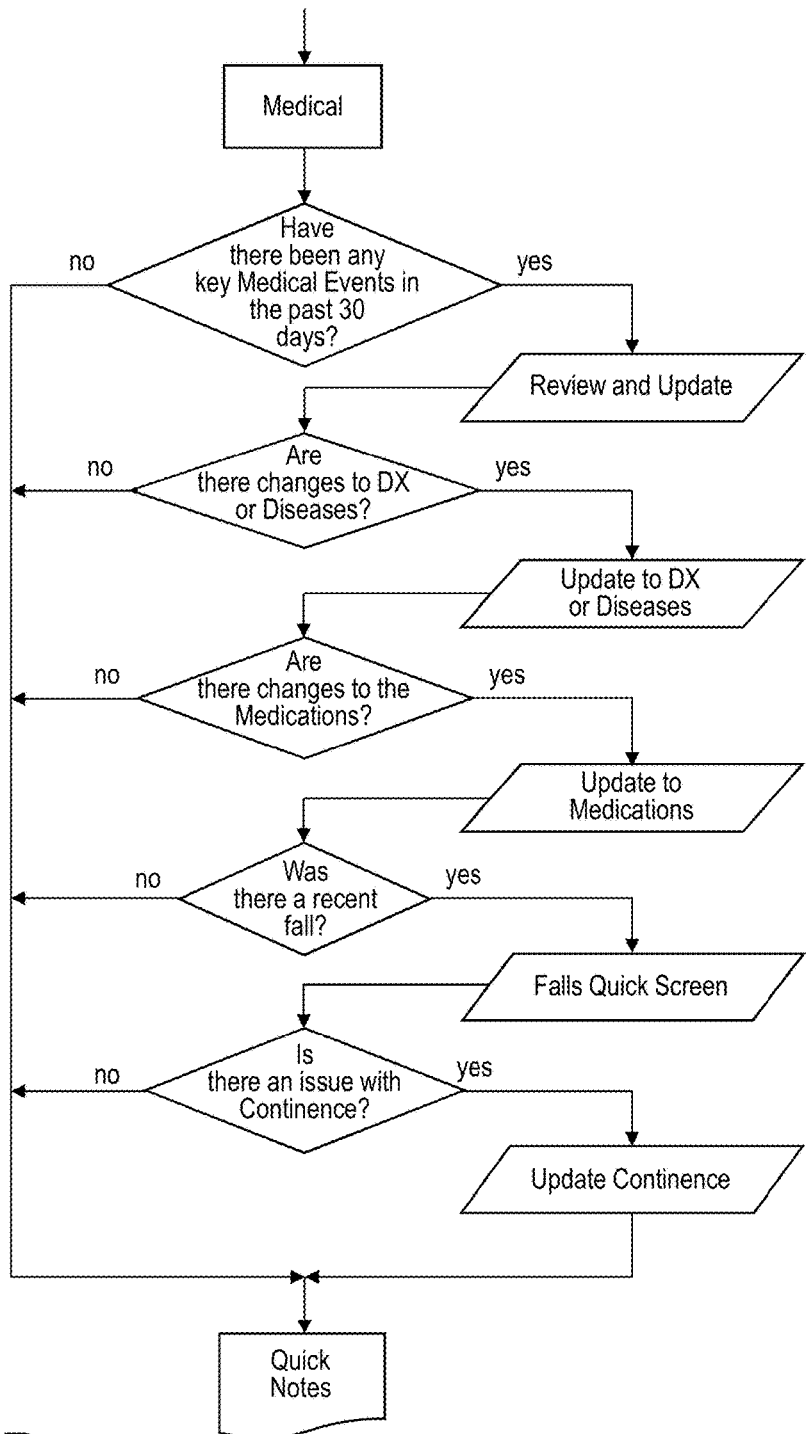
Figure 10:
FIG. 10 is a summary screen as viewed by a registered nurse during a scheduled monthly visit.

On the other hand, a registered nurse accessing the care management system may be presented with a different interface as shown in FIG. 8. Whereas the caregiver's assessments may change day-by-day, the registered nurse is more likely to be interacting with the care management system during regular monthly visits and may follow a more standardized script, such as the workflow depicted in FIGS. 9A-9C. As the registered nurse completes different steps of the process, the registered nurse may be returned to a home interface to identify further actions to be taken, as shown for example in FIG. 10. Thus, the care management system may guide the registered nurse through the activities specified in the nurse's workflow.

Figure 11:
FIG. 11 depicts an exemplary interface for the care management system as viewed by a care manager upon logging into the system for a scheduled visit.
Figure 12A:
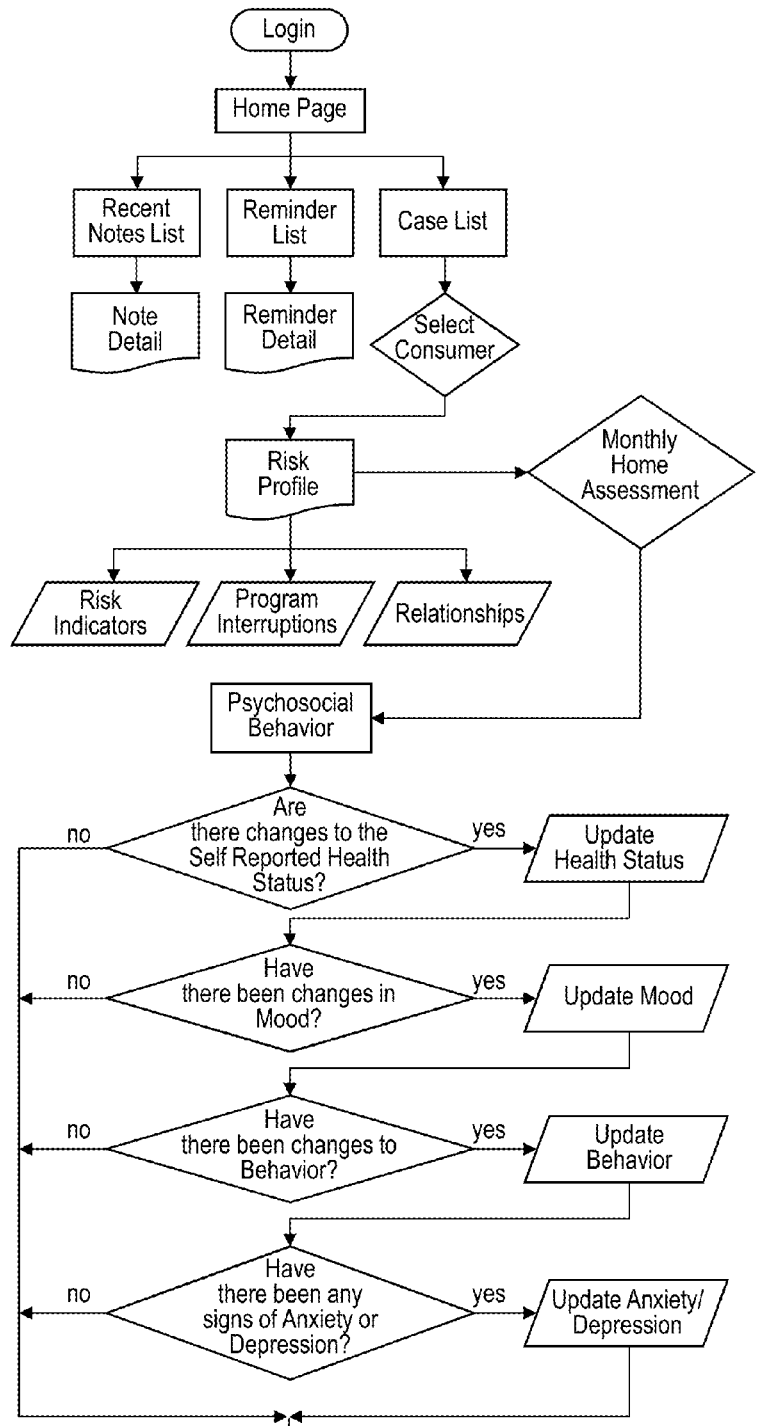
FIGS. 12A-12C depict a flowchart depicting interactions with the care management system by a care manager during a scheduled visit.
Figure 12B:
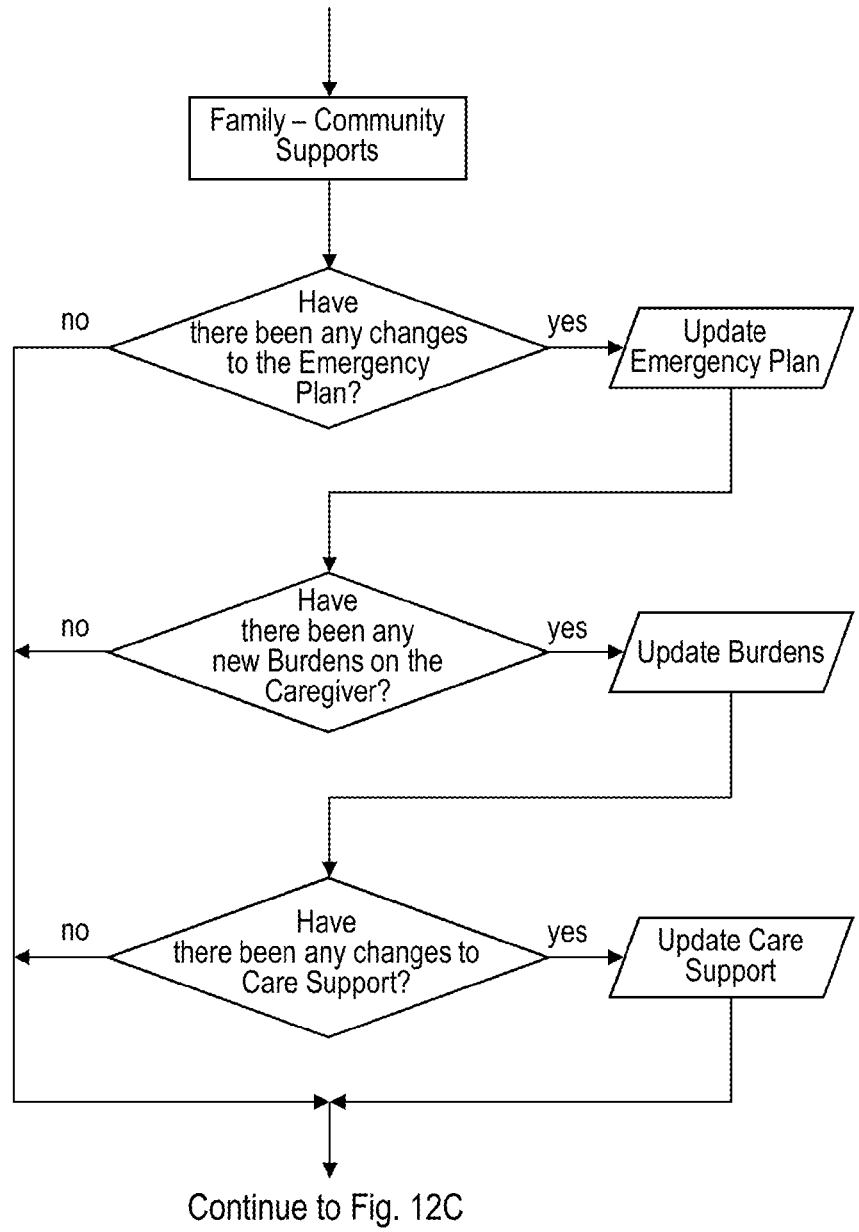
Figure 12C:
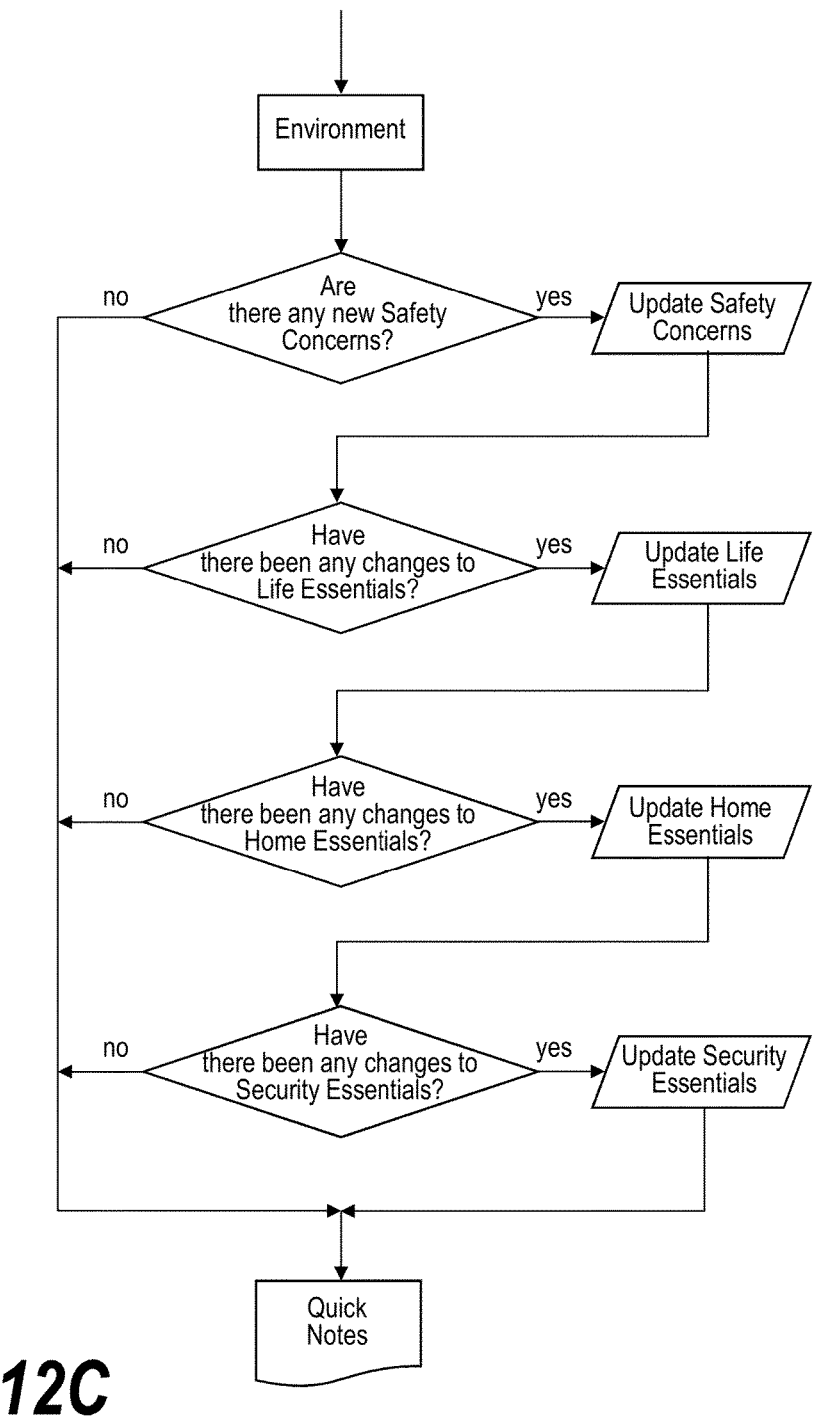

Similarly, FIG. 11 depicts an exemplary interface for a care manager, and FIGS. 12A-12C describe an exemplary workflow to be performed by the care manager. Once again, the home interface of the care management system may guide the care manager through the activities to be performed as specified by the care manager's workflow.

In some embodiments, the data stored in the data storage mechanism 210 may be flagged for different levels of access. The flags may identify an author of the data, users that are authorized to view the data, and/or a domain of the data (e.g., medical, psychosocial, etc.).

Users, such as the caregiver and members of the care management team, may be assigned credentials allowing the users to be authenticated at an assigned level of access and/or to access different domains of data. Depending on the assigned level of access, the domain of the data in question, and/or the identity of the user, different interfaces may be presented by the care management system 200 and different data in the data storage mechanism 210 may be available for inspection.

In some embodiments, the members of the care management team (i.e., contacts excluding the caregiver) may have unrestricted access to all aspects of the care management system 200. In yet further embodiments, levels of access may be different for different members of the care management team. For example, the client's care manager may have unrestricted access to the care management system 200, while the client's social worker may be provided with access to data in the psychosocial and environmental domains but restricted from viewing medical information.

Any entries made by any individual may be protected or flagged as confidential. For example, specific information authored different members of the care management team may be protected from other members of the care management team, if necessary.

Risk Analyzer

The risk analyzer may analyze the information stored by the caregiver and care management team in the data storage mechanism, in order to evaluate the client for risks of particular conditions, and moreover for an overall risk of negative outcomes. The risk analyzer maybe embodied, for example, as hardware or software logic.

The risk analyzer may be configured or programmed to analyze the answers to questions in order to determine particular risk factors. Based on the answers provided, a risk score may be calculated or determined for each domain. For example, the questions in the "functional" domain may be evaluated together in order to generate a risk score in the functional domain, while the questions in the family/community domain may be evaluated together (but separately from the questions in the functional domain) in order to generate a separate risk score for the family/community domain.

The risk analyzer may accept, as an input, information received from contacts through assessments, activity logs, and freeform notes. The contacts may include members of the care management team, which may include a registered nurse, care manager, community care providers such as a primary care physician or social worker, the caregiver, members of the client's family, and the client themselves.

The risk analyzer may assess each subdomain (see FIG. 3) according to industry, regulatory, or proprietary standards in order to generate a score or value for a particular subdomain. The way in which a score for a subdomain is calculated may be dependent on the particular subdomain being evaluated. For example, the answers to frailty questions in the functional domain may be evaluated based on any of a number of well-known frailty indices in order to determine a score for the frailty subdomain of the functional domain.

A specific example in relation to the risk for falls subdomain of the functional domain is described in detail below.

During one or more assessments with the caregiver, the caregiver may answer a plurality of questions from the risk for falls subdomain. The subdomain may be further subdivided into different portions, such as a risk for falling in general, and a risk that (if a fall were to occur) the fall would be injurious. Each possible answer to each question may be assigned a point value. Examples of possible questions and answers include:

Risk for falling (see, e.g., FIGS. 7A-7B):
1. Number of times fallen past 90 days
  a. 0-0 points
  b. 1-1 point
  c. 2+-2 points
2. Timed Get Up and Go Test (TUG):
  a. Under 16 seconds-0 points
  b. Over 15 seconds-1 point
3. Unsteady Gait
  a. None or minimal-0 points
  b. Unsteady-1 point Based on the answers to the questions in the risk for falling portion, a partial subdomain risk may be calculated based on a scale. In this case, 0-1 points may indicate a "low" risk for a fall, while 2+ points may indicate a "high" risk for a fall.

The caregiver may proceed to a further portion of the risk for falling subdomain, which may include questions to determine a risk for an injurious fall. Such questions may include:

4. Age
  a. Under 86 years-0 points
  b. Over 85 years-1 point
5. History of bone fracture or weakness (e.g., Osteoporosis)
  a. No history-0 points
  b. History-1 point
6. Using anticoagulants
  a. No-0 points
  b. Yes-1 point
7. Currently post surgical for thoracic, abdominal or LE problem
  a. No-0 points
  b. Yes-1 point Again, based on the answers to the questions relating to this portion of the sub-domain, a risk for injurious falls may be calculated. In this example, a score of 0-1 points may indicate a low risk for injurious falls, while a score of 2+ points may indicate a high risk for injurious falls.

At any point, the risk for a portion of the subdomain may be requested and displayed in the care management system.

The calculated risks may be displayed for review by a contact. For example, the results calculated above may be displayed on a matrix as depicted in FIG. 7C.

The risk analyzer may retrieve previous calculations for the portion of the sub-domain and compare the previous calculations to determine a trend in the client's risk over time. Based on the calculated score and the trend, the risk analyzer may make one or more recommendations. For example, Based on Quadrant Assignment:
1. Low Risk of falling/Low risk of injury-Monitor
2. High Risk of falling/Low risk of injury-Implement fall reduction interventions
3. Low Risk of falling/High risk of injury-Implement injury prevention interventions
4. High Risk of falling/High risk of injury-Implement fall reduction and injury prevention interventions The risk analyzer may further be programmed with one or more action items based on statistical models and/or clinical results. Based on the answers to questions in other domains and/or subdomains, the risk analyzer may recommend one or more of the action items. For example:

a. Presence of risky medication (e.g., "This patient is on 1 Beers list medication—consider re-evaluation of medication list and discussing with PCP")
b. Presence of any medication that impairs balance (e.g., "Consider Physical Therapy consultation and PCP consultation)
c. Use of assistive device (e.g., "This patient uses a walker and has fallen (x) times in the past 90 days. Consider re-evaluation of assistive device safety by engaging physical therapy or occupational therapy")
d. History of UTI (e.g., "This patient has a history of UTI's and has fallen twice in past 90 days. Consider evaluation of fluid intake and general medical status")
e. Urinary incontinence (e.g., "This patient had a history of urinary incontinence (urgency) and has fallen twice in the past 90 days. Consider re-evaluation of home safety, lighting and medical status")

The risk analyzer may re-evaluate the risk for the portion of the sub-domain at predetermined intervals and/or following key events. In the example of a falls assessment as described above, the risk analyzer may prompt for a new falls risk assessment:

1. At placement
2. Every 6 months
3. After every hospitalization
4. After every injurious fall
5. After 2 non-injurious falls past 90 days
6. After introduction of any Beers list medication Each subdomain may be evaluated based on the answers to questions relating to each portion of the subdomain, and each domain may be evaluated based on the answers to questions for the sub-domains encompassed by the domain. For example, the values calculated for each sub-domain (or portion of a subdomain) may be weighted and aggregated together to calculate an overall score for each domain (or subdomain). The subdomains may be given equal weight in determining a score for the domain, or may be weighted differently based on their importance to the overall risk factor for the domain. The weights may be determined in part based on known statistical models and clinical data for evaluating the risk factors for negative outcomes in a domain, and may be determined in part based on client-specific considerations and attributes.

The calculated risk score for each domain may be modified based on a lexical analysis of unstructured data stored in the care management system. A detailed description of such a lexical analysis is provided below.

Lexical Analysis

In determining the score for the domain, the risk analyzer may analyze the freeform answers and notes using lexical and/or semantic analysis logic. In a lexical analysis, a freeform answer or note may be evaluated to determine whether the text or the context of the freeform answer suggests any risk factors. For example, the system may search the text for keywords that may indicate the presence of a particular condition or problem (e.g., the caregiver used the term "slipped," which may be indicative of a functional or medical problem).

The freeform data is referred to herein as "unstructured" data and is characterized by the open nature of the response or note. Such unstructured data stands in contrast to structured data, such as the answers to questions, which have a finite or quantifiable set of possible responses.

Different types of freeform data may be stored in the care management system. For example, when the registered nurse conducts a monthly home visit, the nurse may answer a series of questions, as described above. Each question may include an option for adding "quick notes" specific to that question. Such quick notes may be stored in the system along with an association or link to the structured data (i.e., the associated question and/or answers to the question).

Each question may be associated with a particular domain, sub domain, and source (e.g., caregiver, care manager, registered nurse). This information forms a structure around each question. In some embodiments, the unstructured data may inherit the structure of any associated structured data. The unstructured data may be associated with, and may inherit from, more than one piece of structured data.

Furthermore, some unstructured data may be unassociated with any structured data. Using the above case of a registered nurse's monthly home visit as an example, the system may give the nurse the option of providing comprehensive freeform clinical documentation regarding the monthly visit. The comprehensive freeform documentation may be stored separately without a link to an associated question.

Thus, the general context in which the unstructured data is collected may provide a first set or level of metadata for the lexical analysis. A second set or level of metadata may be obtained by parsing the text of the freeform notes to identify key words of phrases within the text. These keywords may be added to the first set of metadata for analysis.

The lexical analysis may recognize synonyms for keywords so that, if the user enters a word that is related to a keyword in the system, the lexical analysis can take the synonym into account.

Similarly, the lexical analysis may take into account patterns of words, frequency of term use, and the ordering of terms in determining whether the freeform text indicates the presence of a potential problem or condition.

The lexical analysis may take the client's profile, including the client's conditions and history, into account when analyzing the freeform text. For example, the term "slipped" might indicate a serious problem for someone with a history of balance problems, but might be of less concern for someone without such a history.

The lexical analysis may further take into account any linked structured data, such as answers to questions associated with the freeform data. For example, if the structured data would not, by itself, rise to the level that would require a change in a risk score, the presence of keywords in the linked unstructured freeform data may cause the risk score for that particular question to be changed. Alternatively, if the structured data indicates that a risk score should be changed but mitigating keywords are present in the unstructured freeform data, the risk analyzer may refrain from changing the risk score. Thus, a risk value associated with certain structured data may be at least partially dependent on a lexical analysis of associated unstructured freeform data.

In some embodiments, if the structured data is associated with unstructured freeform data, and general unstructured freeform data not associated with the particular structured data is also provided, then the associated unstructured freeform data may be given increased weight as compared to the general unstructured freeform data. Alternatively or in addition, structured data associated with a particular question may be given reduced weight when considered in a lexical analysis of a risk score unrelated to the question.

By way of example, using the above-described case of a registered nurse's monthly at-home visit, assume that the nurse enters unstructured freeform data that is specifically associated with a question assessing the client's risk for a fall. Further, assume that the nurse enters general clinical notes that are not associated with any particular question. In this example, the unstructured freeform data associated with the falls risk question may be given increased weight in calculating the client's risk score for falls, as compared to the general clinical notes. However, when calculating a risk score unassociated with the client's risk of falling (e.g., when calculating a client's risk of deteriorating community social relations), the unstructured freeform data associated with the falls risk question may be given reduced weight.

In performing the lexical analysis, the mere fact that a caregiver or member of the care management team chose to add freeform notes may be an indication of an unusual condition. For example, if the caregiver rarely enters freeform notes in addition to answering the question presented by the care management system, then the fact that freeform notes were entered on a particular occasion may have increased significance.

Thus, in one embodiment, the care management system may track a frequency at which a user typically enters freeform notes. Upon selecting the option to enter freeform notes, the system may determine whether the user's frequency of entering such notes is below a certain threshold for a predetermined period of time. If so, then any change in the risk score based on a lexical analysis of the freeform notes (either an initial decision to change the risk score or an amount of change to be made) may be given increased weight as compared to a base condition in which the frequency of entering the notes does not fall below the threshold.

One of ordinary skill in the art will recognize that a lexical analysis may be carried out in a number of ways.

Overall Risk Value Calculation and Interventions

After risk values are calculated for each domain and/or are adjusted based on the lexical analysis, an overall risk value may be calculated. The overall risk value may be, for example, a sum of the risk values for each domain. Alternatively, the domains may be weighted differently according to predetermined techniques. For example, the domains may be weighted in favor of domains deemed to be more determinative of potential negative outcomes for a particular client.

Furthermore, domains and sub-domains may be weighted in different ways for the same client depending on what specific risks are under evaluation. For example, a first risk analysis may be run to determine the client's risk of being discharged into a full-time assisted care facility. The first analysis may use a domain/sub-domain weighting that is designed to evaluate for such a risk. A second analysis may use a different weighting in order to evaluate for a risk of premature death (such an analysis might be weighted, for example, more heavily in favor of medical factors than the first analysis).

In evaluating risk, the system may take special notice of risk factors which "move." For example, two different clients with a functional risk score of "$18/20$" may be at the high end of the risk scale. However, if the first client had a functional risk score in the previous month of 19, while the second client had a functional risk score in the previous month of 12, then the system may determine that the second client is a higher risk than the first client. Thus, the magnitude and direction of changes in the client's risk score may be taken into account to indicate a higher or lower overall risk.

The system may take special notice of risk factors which are impactable, over risk factors which are not impactable. For example, the presence of terminal cancer may indicate a high risk, but the risk is typically not impactable—there is nothing to be done about this particular risk. Thus, the system may prioritize risks which can be impacted or altered over risks which cannot be impacted or altered.

The system may also make recommendations for modifying the client's care and/or performing new interventions. The system may be provided, for example, with a database of conditions, recommended actions, and outcomes based on historical data related to the client and caregiver in question and/or other clients and caregivers using the care management system. For example, the database may be programmed with information such as "21% of people in similar condition modified care in way X, and the result was Y." The recommendations may be presented to the caregiver and/or the care management team.

The conditions, actions, and outcomes may be associated with metadata that may be consulted during the lexical analysis. If the lexical analysis of unstructured data associated with the client yields similar keywords to those found in the metadata associated with the conditions, actions, and outcomes, then the system may recommend the associated action with a higher weight than an action without similar associated metadata.

Furthermore, the consumer and caregiver profiles may contain base demographic and clinical information. When unstructured freeform data is entered including similar metadata, the care management system may display similar profiles and interventions previously used by the care management team to achieve improved outcomes.

Based on the individual and/or overall risk scores, client information such as demographics as reflected in the client's profile, and/or statistical models, the system may make risk predictions tailored to the client. For example, the system may indicate that, given the client's history and the prominence of a particular condition in a population with similar characteristics to the client, the client is at high risk for the condition. In formulating recommendations, as in calculating the risk score, the movement and impactability of the risk factors may be taken into account.

A non-limiting example of an overall risk score calculation is shown below.

The overall risk in this example ranges from 0-100 and is comprised of 5 Domain scores, weighted equally, with scores ranging from 0-20. Each Domain risk score is constructed using "scales" reflecting responses to "core" and "derived" assessment questions. Domain score construction iterates over time based on statistical risk modeling techniques (regression).

TABLE 1

Medical Domain

| % of Total for Domain | Scale | Contribution to Overall Score |
|---|---|---|
| 10% | Age | 2 |
| 10% | Medication Count | 2 |
| 10% | Risky Medications | 2 |
| 10% | Diagnosis Total | 2 |
| 15% | Institutional Risk CAP (interRAI - MDS) is triggered | 3 |

TABLE 1-continued

Medical Domain

| % of Total for Domain | Scale | Contribution to Overall Score |
|---|---|---|
| 25% | Has been Hospitalized | 5 |
| 10% | Fall Risk (any Quadrant > 1) | 2 |
| 10% | Has Fallen | 2 |
| 100% | | 20 |

TABLE 2

Functional Domain

| % of Total for Domain | Scale | Contribution to Overall Score |
|---|---|---|
| 40% | High ADL Count | 8 |
| 40% | ADL Hierarchy (interRAI - MDS) | 8 |
| 20% | IADL CAP (interRAI - MDS) | 4 |
| 100% | | 20 |

TABLE 3

Psychosocial Domain

| % of Total for Domain | Scale | Contribution to Overall Score |
|---|---|---|
| 15% | Behavior CAP (interRAI - MDS) | 3 |
| 5% | Depression/Anxiety | 1 |
| 10% | Communication (interRAI - MDS) | 2 |
| 20% | Cognitive Performance Scale (interRAI - MDS) | 4 |
| 20% | Has Psych Diagnosis - Any | 4 |
| 30% | Monthly Home Visit Score greater than 5 | 6 |
| 100% | | 20 |

TABLE 4

Community Domain

| Scale | Criterion | Contribution to Overall Score |
|---|---|---|
| Have there been any changes in your important relationships since we last met? | Yes | 1 |
| Have there been any changes in your relationships with (patient) since we last met? | | 0 |
| Caregiver: How often do you feel lonely or alone? | | 1 |
| Caregiver General health rating | Poor or Low | 2 |
| Caregiver: Rapid changes to cognition, memory, mental status | Any change | 2 |
| Patient decision making | Any change | 2 |
| Caregiver Depression Screen | 0-1 | 0 |
| | 2-3 | 1 |
| | 4-5 | 2 |
| Caregiver Anxiety Screen | 0-1 | 0 |
| | 2-3 | 1 |
| | 4-5 | 2 |
| Patient Psychotropic med adherence | N/A or Good | 0 |
| | Poor | 1 |
| Patient Wandering | Yes | 1 |
| Patient Verbal Abuse | Yes | 1 |

TABLE 4-continued

Community Domain

| Scale | Criterion | Contribution to Overall Score |
|---|---|---|
| Patient Physical Abuse | Yes | 1 |
| Patient Sexually Inappropriate Behavior | Yes | 1 |
| Patient Care Resistance | Yes | 1 |

TABLE 5

Environment Domain

| Scale | Criterion | Contribution to Overall Score |
|---|---|---|
| CGH Home Assessment: Any changes in the home environment that might preclude continued placement (consider regulatory and safety) | Yes | 3 |
| Home Essentials: Any changes that might affect your ability to live with patient at home? | Yes | 10 |
| Life Essentials: Are there adequate supplies of food? | Yes | 1 |
| Life Essentials: Are you and the patient warm/cool enough? | Yes | 1 |
| Security Essentials: Any new community threats? | Yes | 1 |
| Security Essentials: Anyone new in the home? | Yes | 4 |

In addition to the overall risk scores described above, specific risk scores may be calculated to provide a real time snapshot for the overall risk of predefined events. Specific risk scores may be calculated, using regression based on statistical models and/or clinical data, for key outcomes. Some non-limiting examples of specific risk scores include:

a. Risk for hospitalization next 90 days: (weighting) Medical risk domain score+(weighting) Functional risk domain score+(weighting) Caregiver burden scale=risk of hospitalization risk next 90 days b. Risk for re-hospitalization next 30 days: (weighting) Discharge diagnosis+(weighting) Health Literacy+ (weighting) Patient activation score+(weighting) Patient medication adherence score+(weighting) Count hospitalizations past 180 days=risk for re-hospitalization next 30 days c. Risk for re-hospitalization next 30 days with CHF as primary diagnosis: (weighting) Risk for re-hospitalization next 30 days score+(weighting) Increase in any 2 of these symptoms in last 10 days: SOB, swelling legs/feet, fatigue, sleep problems, loss of appetite, tender abdomen, productive cough, increased nighttime urination, confusion, memory impairment=risk for rehospitalization next 30 days with CHF d. Risk for low patient satisfaction rating on "Caregiver Homes has changed my life"<Agree/Strongly Agree: (weighting) Care Manager activation score+(weighting) Consumer activation score+(weighting) Consumer rating of general health+(weighting) Functional Risk Domain score=Risk for low patient satisfaction The subdomain, domain, and specific risk scores may be presented to the caregiver and/or care management team on an interface, such as the interface depicted in FIG. 13. A quantitative and/or qualitative risk score may be depicted for each domain, subdomain, or portion of a subdomain. Risk scores may be depicted in conjunction with an indicator, such as a graphical indicator, showing any recent trends in the risk score. The graphical indicator may distinguish trends, for example, using an arrow or by changing colors.

The risk factors may also be presented in context on a summary of the client's status, as shown for example in FIG. 14.

Exemplary Electronic Device Implementation

Figure 15:
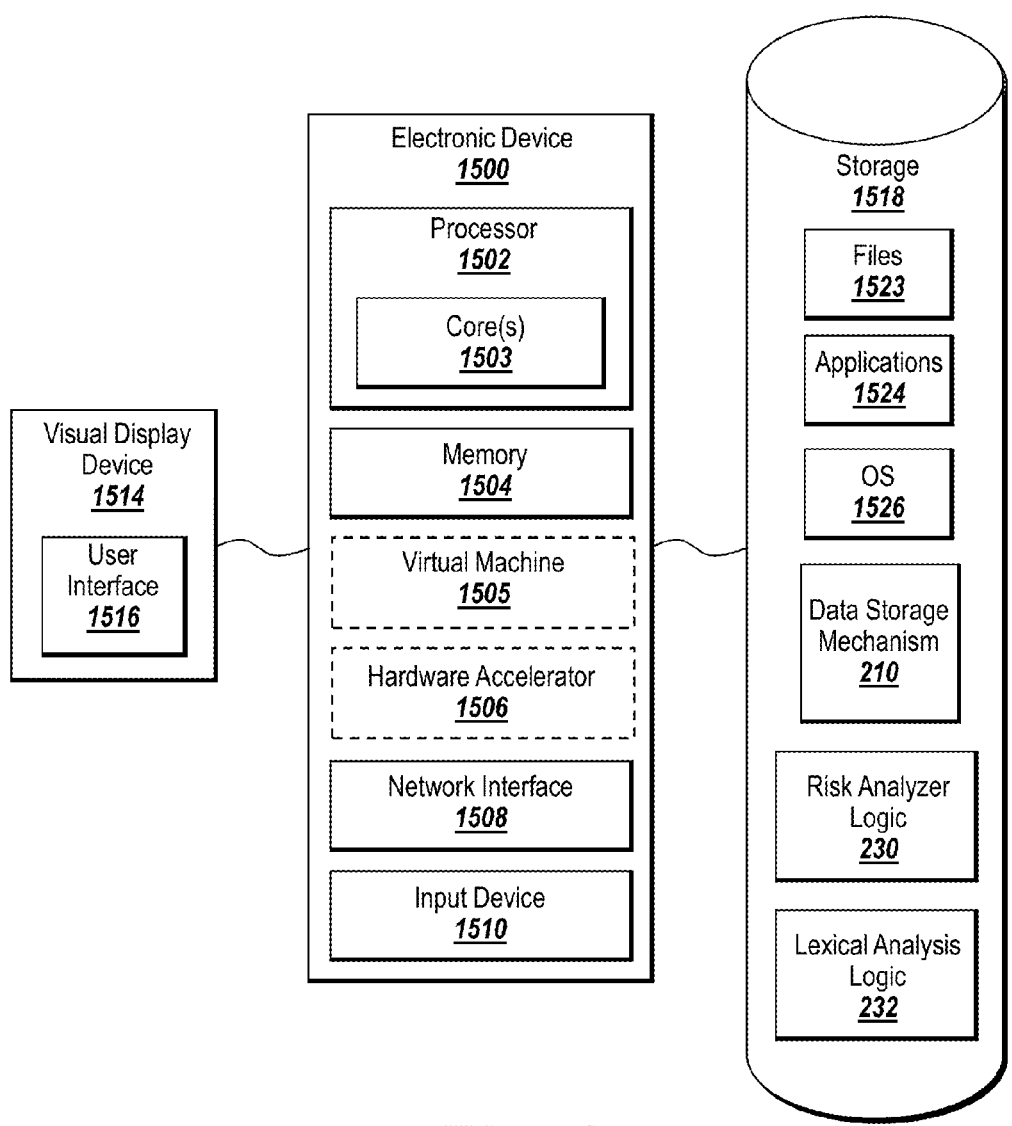
FIG. 15 is a block diagram depicting an exemplary electronic computing device suitable for use with exemplary embodiments of the present invention.

One or more of the above-described acts may be encoded as computer-executable instructions executable by processing logic. The computer-executable instructions may be stored on one or more non-transitory computer readable media. One or more of the above described acts may be performed in a suitably-programmed electronic device. FIG. 15 depicts an example of an electronic device 1500 that may be suitable for use with one or more acts disclosed herein.

The electronic device 1500 may take many forms, including but not limited to a computer, workstation, server, network computer, quantum computer, optical computer, Internet appliance, mobile device, a pager, a tablet computer, a smart sensor, application specific processing device, etc.

The electronic device 1500 is illustrative and may take other forms. For example, an alternative implementation of the electronic device 1500 may have fewer components, more components, or components that are in a configuration that differs from the configuration of FIG. 6. The components of FIG. 6 and/or other figures described herein may be implemented using hardware based logic, software based logic and/or logic that is a combination of hardware and software based logic (e.g., hybrid logic); therefore, components illustrated in FIG. 6 and/or other figures are not limited to a specific type of logic.

The processor 1502 may include hardware based logic or a combination of hardware based logic and software to execute instructions on behalf of the electronic device 1500. The processor 1502 may include logic that may interpret, execute, and/or otherwise process information contained in, for example, the memory 1504. The information may include computer-executable instructions and/or data that may implement one or more embodiments of the invention. The processor 1502 may comprise a variety of homogeneous or heterogeneous hardware. The hardware may include, for example, some combination of one or more processors, microprocessors, field programmable gate arrays (FPGAs), application specific instruction set processors (ASIPs), application specific integrated circuits (ASICs), complex programmable logic devices (CPLDs), graphics processing units (GPUs), or other types of processing logic that may interpret, execute, manipulate, and/or otherwise process the information. The processor may include a single core or multiple cores 1503. Moreover, the processor 1502 may include a system-on-chip (SoC) or system-in-package (SiP).

The electronic device 1500 may include one or more tangible non-transitory computer-readable storage media for storing one or more computer-executable instructions or software that may implement one or more embodiments of the invention. The non-transitory computer-readable storage media may be, for example, the memory 1504 or the storage 1518. The memory 11504 may comprise a RAM that may include RAM devices that may store the information. The RAM devices may be volatile or non-volatile and may include, for example, one or more DRAM devices, flash memory devices, SRAM devices, zero-capacitor RAM (ZRAM) devices, twin transistor RAM (TTRAM) devices, read-only memory (ROM) devices, ferroelectric RAM (Fe-RAM) devices, magneto-resistive RAM (MRAM) devices, phase change memory RAM (PRAM) devices, or other types of RAM devices.

One or more computing devices 1500 may include a virtual machine (VM) 1505 for executing the instructions loaded in the memory 1504. A virtual machine 1505 may be provided to handle a process running on multiple processors so that the process may appear to be using only one computing resource rather than multiple computing resources. Virtualization may be employed in the electronic device 1500 so that infrastructure and resources in the electronic device may be shared dynamically. Multiple VMs 1505 may be resident on a single computing device 1500.

A hardware accelerator 1506, may be implemented in an ASIC, FPGA, or some other device. The hardware accelerator 1506 may be used to reduce the general processing time of the electronic device 1500.

The electronic device 1500 may include a network interface 1508 to interface to a Local Area Network (LAN), Wide Area Network (WAN) or the Internet through a variety of connections including, but not limited to, standard telephone lines, LAN or WAN links (e.g., T1, T3, 56 kb, X.25), broadband connections (e.g., integrated services digital network (ISDN), Frame Relay, asynchronous transfer mode (ATM), wireless connections (e.g., 802.11), high-speed interconnects (e.g., InfiniBand, gigabit Ethernet, Myrinet) or some combination of any or all of the above. The network interface 1508 may include a built-in network adapter, network interface card, personal computer memory card international association (PCMCIA) network card, card bus network adapter, wireless network adapter, universal serial bus (USB) network adapter, modem or any other device suitable for interfacing the electronic device 1500 to any type of network capable of communication and performing the operations described herein.

The electronic device 1500 may include one or more input devices 1510, such as a keyboard, a multi-point touch interface, a pointing device (e.g., a mouse), a gyroscope, an accelerometer, a haptic device, a tactile device, a neural device, a microphone, or a camera that may be used to receive input from, for example, a user. Note that electronic device 1500 may include other suitable I/O peripherals.

The input devices 1510 may allow a user to provide input that is registered on a visual display device 1514. A graphical user interface (GUI) 1516 may be shown on the display device 1514.

A storage device 1518 may also be associated with the computer 1500. The storage device 1518 may be accessible to the processor 1502 via an I/O bus. The information may be executed, interpreted, manipulated, and/or otherwise processed by the processor 1502. The storage device 1518 may include, for example, a storage device, such as a magnetic disk, optical disk (e.g., CD-ROM, DVD player), random-access memory (RAM) disk, tape unit, and/or flash drive. The information may be stored on one or more non-transient tangible computer-readable media contained in the storage device. This media may include, for example, magnetic discs, optical discs, magnetic tape, and/or memory devices (e.g., flash memory devices, static RAM (SRAM) devices, dynamic RAM (DRAM) devices, or other memory devices). The information may include data and/or computer-executable instructions that may implement one or more embodiments of the invention The storage device 1518 may further store files 1523, applications 1524, and the electronic device 1500 can be running an operating system (OS) 1526. Examples of OS 1526 may include the Microsoft® Windows® operating systems, the Unix and Linux operating systems, the MacOS® for Macintosh computers, an embedded operating system, such as the Symbian OS, a real-time operating system, an open source operating system, a proprietary operating system, operating systems for mobile electronic devices, or other operating system capable of running on the electronic device and performing the operations described herein. The operating system may be running in native mode or emulated mode.

The storage device 1518 may further include a data storage mechanism 210 for storing notes, questions, and answers, as discussed above in more detail with respect to FIG. 2.

Furthermore, the storage device 1518 may store risk analyzer logic 230 and lexical analysis logic 232. The risk analyzer logic 230 may compute weighted or unweighted scores based on the risk factors identified in the assessments (see FIG. 15). For example, each domain may be associated with a score, and the risk analyzer logic 230 may calculate the score for each domain according to a formula. The formula may be, for example, a formula developed by an industry or professional group for evaluating a domain (e.g., a frailty index, etc.), or may be based on an assessment performed by the client's caregiver, nurse, social worker, etc. evaluated on a scale (e.g., 1-10). The risk analyzer logic 230 way weight and add these scores to arrive at an overall risk assessment The lexical analysis logic 232 may include logic for reviewing freeform text, such as those present in the notes in the data storage mechanism 210 (see FIG. 2). For example, the lexical analysis logic 232 may review the notes for keywords, synonyms of keywords, and/or combinations of words that may indicate a problem with the client or a potential problem that may arise in the future.

The output of the risk logic 230 and/or the lexical analysis logic 232 may be used to make recommendations for the care of the client.

One or more embodiments of the invention may be implemented using computer-executable instructions and/or data that may be embodied on one or more non-transitory tangible computer-readable mediums. The mediums may be, but are not limited to, a hard disk, a compact disc, a digital versatile disc, a flash memory card, a Programmable Read Only Memory (PROM), a Random Access Memory (RAM), a Read Only Memory (ROM), Magnetoresistive Random Access Memory (MRAM), a magnetic tape, or other computer-readable media.

Figure 16:
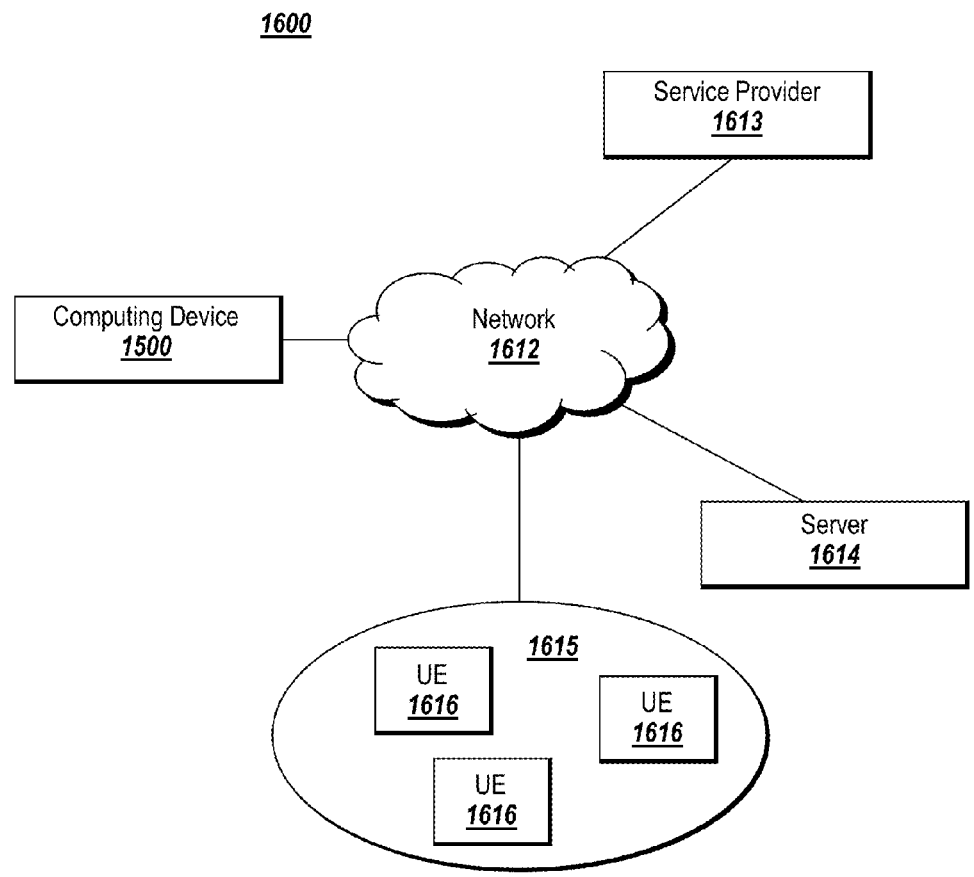
FIG. 16 is a block diagram depicting an exemplary network-based embodiment suitable for use with exemplary embodiments of the present invention.

FIG. 16 depicts a network implementation that may implement one or more embodiments of the invention. A system 1600 may include a computing device 1500, a network 1612, a service provider 1613, a target environment 1614, and a cluster 1615. The embodiment of FIG. 16 is exemplary, and other embodiments can include more devices, fewer devices, or devices in arrangements that differ from the arrangement of FIG. 16.

The network 1612 may transport data from a source to a destination. Embodiments of the network 1612 may use network devices, such as routers, switches, firewalls, and/or servers (not shown) and connections (e.g., links) to transport data. Data may refer to any type of machine-readable information having substantially any format that may be adapted for use in one or more networks and/or with one or more devices (e.g., the computing device 1500, the service provider 1613, etc.). Data may include digital information or analog information. Data may further be packetized and/or non-packetized.

The network 1612 may be a hardwired network using wired conductors and/or optical fibers and/or may be a wireless network using free-space optical, radio frequency (RF), and/or acoustic transmission paths. In one implementation, the network 1612 may be a substantially open public network, such as the Internet. In another implementation, the network 1612 may be a more restricted network, such as a corporate virtual network. The network 1612 may include Internet, intranet, Local Area Network (LAN), Wide Area Network (WAN), Metropolitan Area Network (MAN), wireless network (e.g., using IEEE 802.11), or other type of network The network 1612 may use middleware, such as Common Object Request Broker Architecture (CORBA) or Distributed Component Object Model (DCOM). Implementations of networks and/or devices operating on networks described herein are not limited to, for example, any particular data type, protocol, and/or architecture/configuration.

The service provider 1613 may include a device that makes a service available to another device. For example, the service provider 1613 may include an entity (e.g., an individual, a corporation, an educational institution, a government agency, etc.) that provides one or more services to a destination using a server and/or other devices. Services may include instructions that are executed by a destination to perform an operation (e.g., an optimization operation). Alternatively, a service may include instructions that are executed on behalf of a destination to perform an operation on the destination's behalf.

The server 1614 may include a device that receives information over the network 1612. For example, the server 1614 may be a device that receives user input from the computer 1500.

The cluster 1615 may include a number of units of execution (UEs) 1616 and may perform processing on behalf of the computer 1500 and/or another device, such as the service provider 1613 or server 1614. For example, the cluster 1615 may perform parallel processing on an operation received from the computer 1500. The cluster 1615 may include UEs 1616 that reside on a single device or chip or that reside on a number of devices or chips.

The units of execution (UEs) 1616 may include processing devices that perform operations on behalf of a device, such as a requesting device. A UE may be a microprocessor, field programmable gate array (FPGA), and/or another type of processing device. UE 1616 may include code, such as code for an operating environment. For example, a UE may run a portion of an operating environment that pertains to parallel processing activities. The service provider 1613 may operate the cluster 1615 and may provide interactive optimization capabilities to the computer 1500 on a subscription basis (e.g., via a web service).

Units of Execution (UEs) may provide remote/distributed processing capabilities for the applications 1524. A hardware unit of execution may include a device (e.g., a hardware resource) that may perform and/or participate in parallel programming activities. For example, a hardware unit of execution may perform and/or participate in parallel programming activities in response to a request and/or a task it has received (e.g., received directly or via a proxy). A hardware unit of execution may perform and/or participate in substantially any type of parallel programming (e.g., task, data, stream processing, etc.) using one or more devices. For example, a hardware unit of execution may include a single processing device that includes multiple cores or a number of processors. A hardware unit of execution may also be a programmable device, such as a field programmable gate array (FPGA), an application specific integrated circuit (ASIC), a digital signal processor (DSP), or other programmable device. Devices used in a hardware unit of execution may be arranged in many different configurations (or topologies), such as a grid, ring, star, or other configuration. A hardware unit of execution may support one or more threads (or processes) when performing processing operations.

A software unit of execution may include a software resource (e.g., a technical computing environment) that may perform and/or participate in one or more parallel programming activities. A software unit of execution may perform and/or participate in one or more parallel programming activities in response to a receipt of a program and/or one or more portions of the program. A software unit of execution may perform and/or participate in different types of parallel programming using one or more hardware units of execution. A software unit of execution may support one or more threads and/or processes when performing processing operations.

The term 'parallel programming' may be understood to include multiple types of parallel programming, e.g. task parallel programming, data parallel programming, and stream parallel programming. Parallel programming may include various types of processing that may be distributed across multiple resources (e.g., software units of execution, hardware units of execution, processors, microprocessors, clusters, labs) and may be performed at the same time.

For example, parallel programming may include task parallel programming where a number of tasks may be processed at the same time on a number of software units of execution. In task parallel programming, a task may be processed independently of other tasks executing, for example, at the same time.

Parallel programming may include data parallel programming, where data (e.g., a data set) may be parsed into a number of portions that may be executed in parallel using, for example, software units of execution. In data parallel programming, the software units of execution and/or the data portions may communicate with each other as processing progresses.

Parallel programming may include stream parallel programming (sometimes referred to as pipeline parallel programming). Stream parallel programming may use a number of software units of execution arranged, for example, in series (e.g., a line) where a first software unit of execution may produce a first result that may be fed to a second software unit of execution that may produce a second result given the first result. Stream parallel programming may also include a state where task allocation may be expressed in a directed acyclic graph (DAG) or a cyclic graph.

Other parallel programming techniques may involve some combination of task, data, and/or stream parallel programming techniques alone or with other types of processing techniques to form hybrid-parallel programming techniques.

The foregoing description may provide illustration and description of various embodiments of the invention, but is not intended to be exhaustive or to limit the invention to the precise form disclosed. Modifications and variations may be possible in light of the above teachings or may be acquired from practice of the invention. For example, while a series of acts has been described above, the order of the acts may be modified in other implementations consistent with the principles of the invention. Further, non-dependent acts may be performed in parallel.

In addition, one or more implementations consistent with principles of the invention may be implemented using one or more devices and/or configurations other than those illustrated in the Figures and described in the Specification without departing from the spirit of the invention. One or more devices and/or components may be added and/or removed from the implementations of the figures depending on specific deployments and/or applications. Also, one or more disclosed implementations may not be limited to a specific combination of hardware.

Furthermore, certain portions of the invention may be implemented as logic that may perform one or more functions. This logic may include hardware, such as hardwired logic, an application-specific integrated circuit, a field programmable gate array, a microprocessor, software, or a combination of hardware and software.

No element, act, or instruction used in the description of the invention should be construed critical or essential to the invention unless explicitly described as such.

Also, as used herein, the article "a" is intended to include one or more items. Where only one item is intended, the term "a single" or similar language is used. Further, the phrase "based on," as used herein is intended to mean "based, at least in part, on" unless explicitly stated otherwise. In addition, the term "user", as used herein, is intended to be broadly interpreted to include, for example, an electronic device (e.g., a workstation) or a user of an electronic device, unless otherwise stated.

It is intended that the invention not be limited to the particular embodiments disclosed above, but that the invention will include any and all particular embodiments and equivalents falling within the scope of the following appended claims.

The invention claimed is:

1. A computer-implemented method for monitoring and assessing the healthcare of a patient, comprising:
   obtaining selected healthcare information of the patient,
   selecting, using a processor of a computer, one or more questions from a question database, the question database being stored in a storage element and comprising structured questions and a plurality of structured answers for each question and being subdivided into a plurality of domains related to home-based care of a client, wherein the questions are selected in a custom order by a risk analyzer based on known information about the client's risk for conditions evaluated by the questions;
   acquiring selected healthcare information of the patient at selected intervals by presenting the selected questions on a display device;
   receiving a selection of one or more answers from among the plurality of structured answers;
   receiving unstructured data in the form of free form notes from a caregiver and the risk analyzer performs a lexical analysis on the unstructured data and generates a lexical result to improve the speed of the processor of the computer;
   providing the selected one or more answers and the lexical result to the risk analyzer to calculate risk scores based on the one or more answers and the lexical result for each of the plurality of domains,
   wherein each of the plurality of domains includes a plurality of sub-domains, and wherein each of the plurality of sub-domains has a risk score associated therewith, and the risk score for each of the plurality of domains is a combination of the risk scores of the sub-domains associated therewith, and wherein the risk analyzer determines an overall risk score from a combination of the risk scores from the plurality of domains, and
   monitoring the risk scores of the plurality of domains or the overall risk score to determine if the risk score changes over time, and then initiating a healthcare action if the risk score changes over time, and
   displaying the risk score on the display device.

2. The method of claim 1, wherein the plurality of domains are selected from a group consisting of:
   a functional domain relating to an ability of the client to function in daily life;
   a medical domain relating to a medical status of the client;
   a psychosocial/behavioral domain relating to a mental status of the client;
   a family/community domain relating to a family and community support network of the client; and
   an environmental domain relating to a client's immediately daily environment and physical security.

3. The method of claim 1, wherein the questions are presented iteratively over a period of time in order to build a representation of the client's risk factors.

4. The method of claim 1, wherein the risk analyzer determines, based on a calculation of the client's risk factors, follow-up or triggered questions to be presented on the interface.

5. The method of claim 1, wherein a plurality of the questions or the domains are each associated with a user having experience relating to the domain or the question with respect to the client, and the questions are selected by the risk analyzer based on an identity of the user logged into the interface.

6. A system for monitoring and assessing the healthcare of a patient, comprising:
   a non-transitory storage medium storing a question database, the question database comprising structured questions and a plurality of structured answers for each question and being subdivided into a plurality of domains related to home-based care of a client; and
   a processor configured to:
      select one or more questions from the question database, wherein the questions are selected in a custom order by a risk analyzer based on known information about the client's risk for conditions evaluated by the questions;
      present the selected questions on an interface;
      receive a selection of one or more answers from among the plurality of structured answers;
      receive unstructured data in the form of free form notes from a caregiver and the risk analyzer performs a lexical analysis on the unstructured data and generates a lexical result to improve the speed of the processor of the computer; and
      provide the selected one or more answers and the lexical result to the risk analyzer to calculate risk scores for the plurality of domains based on the one or more answers and the lexical result;
      wherein each of the plurality of domains includes a plurality of sub-domains, and wherein each of the plurality of sub-domains has a risk score associated therewith, and the risk score for each of the plurality of domains is a combination of the risk scores of the sub-domains associated therewith, and wherein the risk analyzer determines an overall risk score from a combination of the risk scores from the plurality of domains,
   means for monitoring the risk scores of the plurality of domains or the overall risk score to determine if the risk score changes over time, and then initiating a selected healthcare action if the risk score changes over time, and
   a display device for displaying the risk score.

7. The system of claim 6, wherein the plurality of domains are selected from a group consisting of:

a functional domain relating to an ability of the client to function in daily life;

a medical domain relating to a medical status of the client;

a psychosocial/behavioral domain relating to a mental status of the client;

a family/community domain relating to a family and community support network of the client; and an environmental domain relating to a client's immediately daily environment and physical security.

8. The system of claim 6, wherein the questions are presented iteratively over a period of time in order to build a representation of the client's risk factors.

9. The system of claim 6, wherein the risk analyzer determines, based on a calculation of the client's risk factors, follow-up or triggered questions to be presented on the interface.

10. The system of claim 6, wherein a plurality of the questions or the domains are each associated with a user having experience relating to the domain or the question with respect to the client, and the questions are selected by the risk analyzer based on an identity of the user logged into the interface.

11. The method of claim 1, wherein the processor weights the risk scores of the sub-domains associated with a particular domain differently when determining the risk score of the particular domain.

12. The method of claim 1, wherein the risk score for each of the plurality of sub-domains includes a combination of risk scores associated with structured data and unstructured data.

13. The method of claim 12, wherein the unstructured data includes freeform notes.

* * * * *